United States Patent [19]

Gerwick et al.

[11] Patent Number: 5,324,739
[45] Date of Patent: Jun. 28, 1994

[54] COMPOUND EXHIBITING ANTIPROLIFERATIVE ACTIVITY AGAINST CELLS

[75] Inventors: William H. Gerwick; Philip J. Proteau; Dale G. Nagle, all of Corvallis, Oreg.

[73] Assignee: State of Oregon Acting by and Through the State Board of Higher Education on Behalf of Oregon State University, Eugene, Oreg.

[21] Appl. No.: 134,282

[22] Filed: Oct. 7, 1993

[51] Int. Cl.$^5$ .................. A61K 31/425; C07D 277/10
[52] U.S. Cl. .................................... 514/365; 548/146
[58] Field of Search ...................... 548/146; 514/365

[56] References Cited

PUBLICATIONS

Jütten et al., Tetrahedron vol. 43 No. 8, pp. 4133–4140 (1987).

*Primary Examiner*—Joseph Paul Brust
*Assistant Examiner*—MarySusan H. Gabilen
*Attorney, Agent, or Firm*—Klarquist Sparkman Campbell Leigh & Whinston

[57] ABSTRACT

Isomers of a cytotoxic compound isolated and purified from a marine cyanobacterium *Lyngbya majuscula* are disclosed. The isomers termed Curacin A and Curacin B exhibits substantial biological activity against proliferating cells. The Curacin A and Curacin B isomers appear to be antimitotics. Methods for using the isomers are also disclosed.

6 Claims, 26 Drawing Sheets

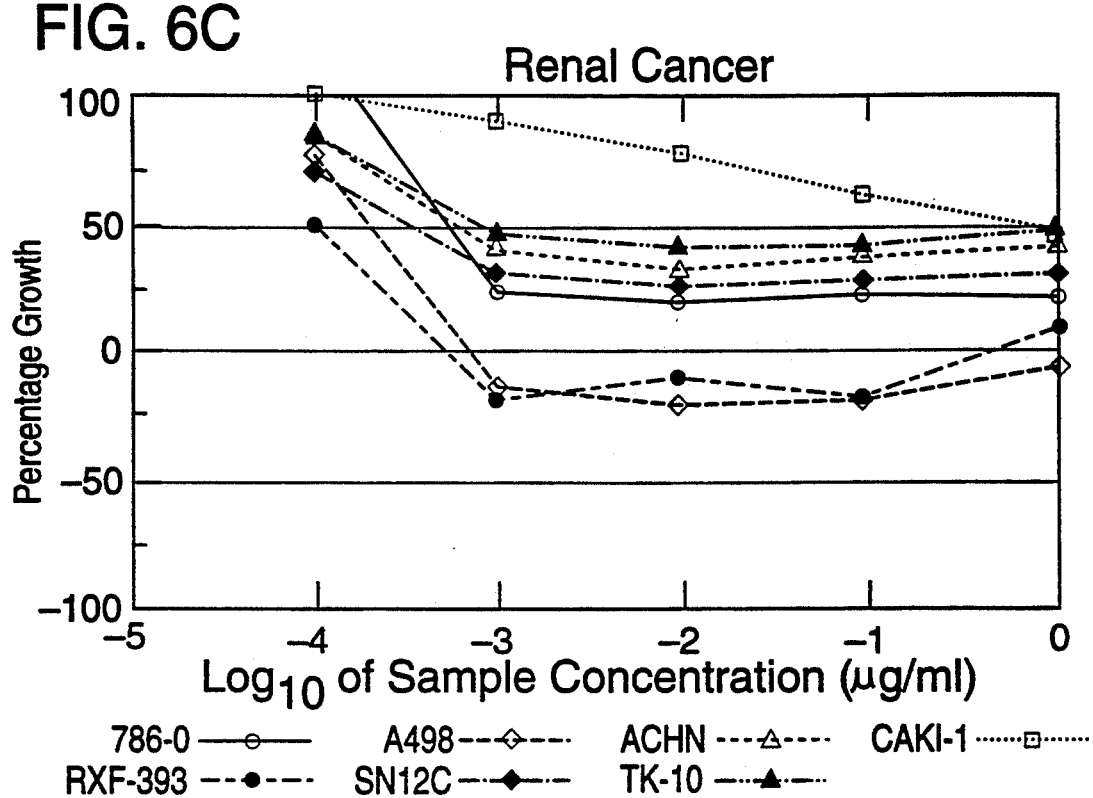
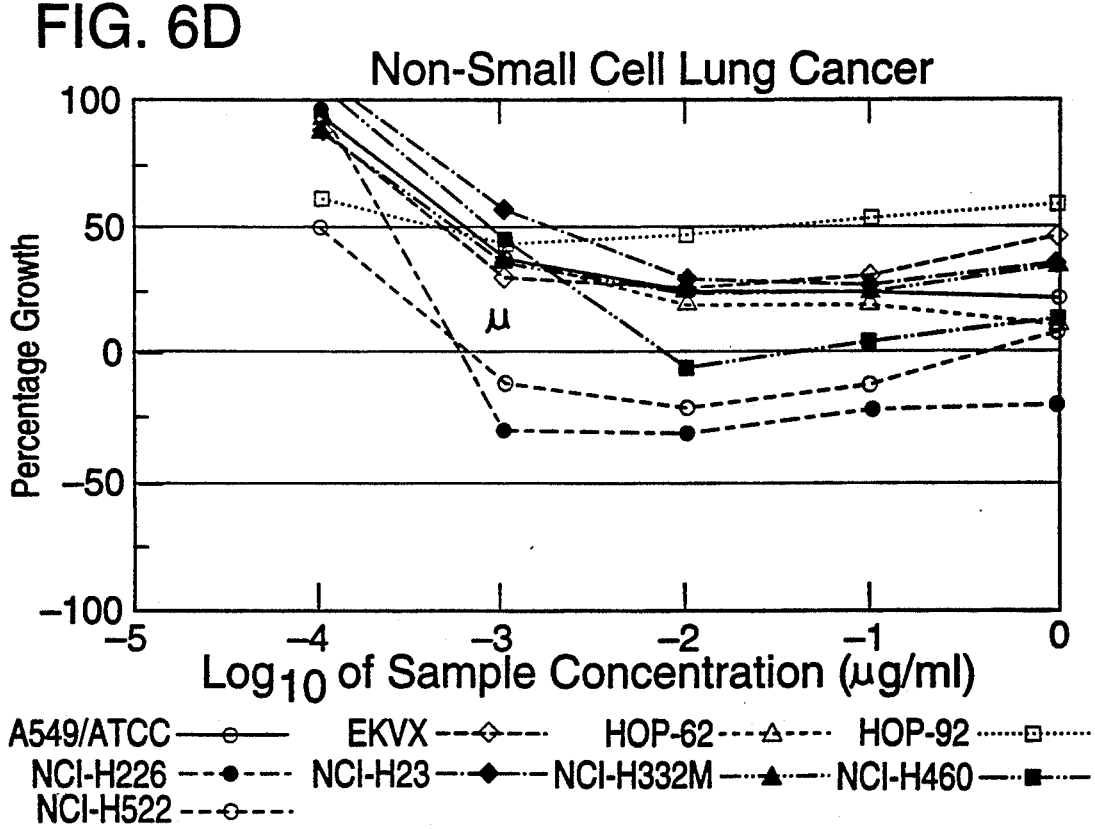

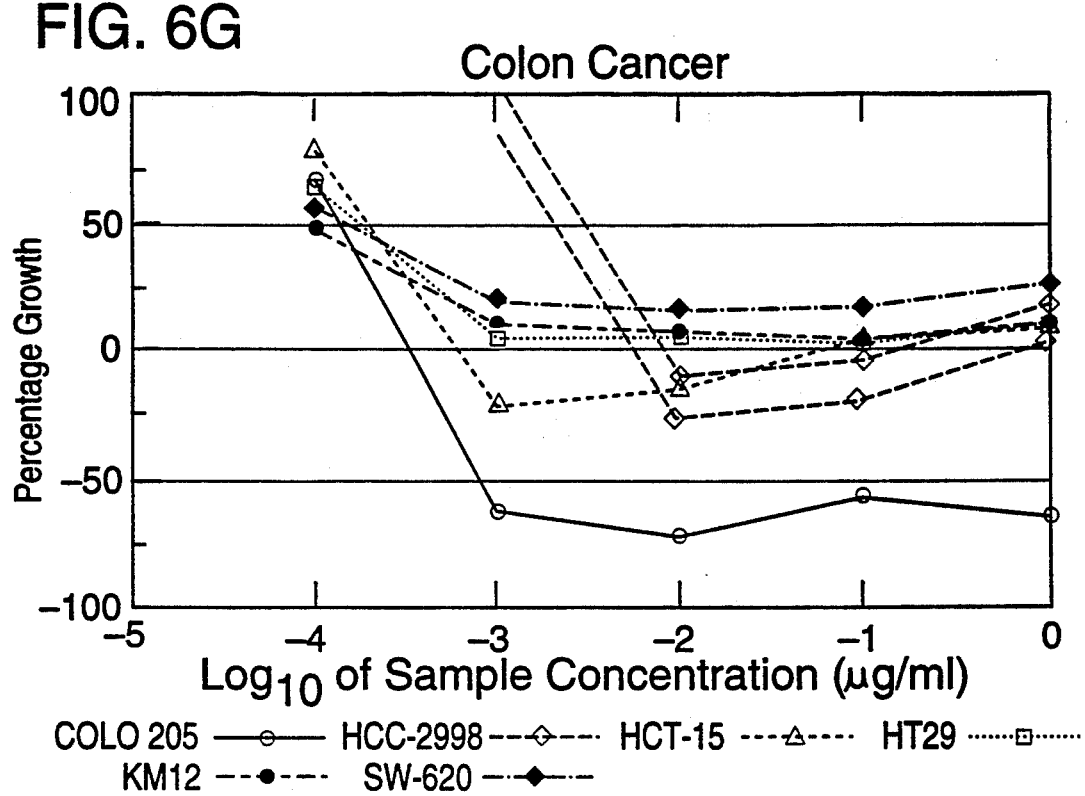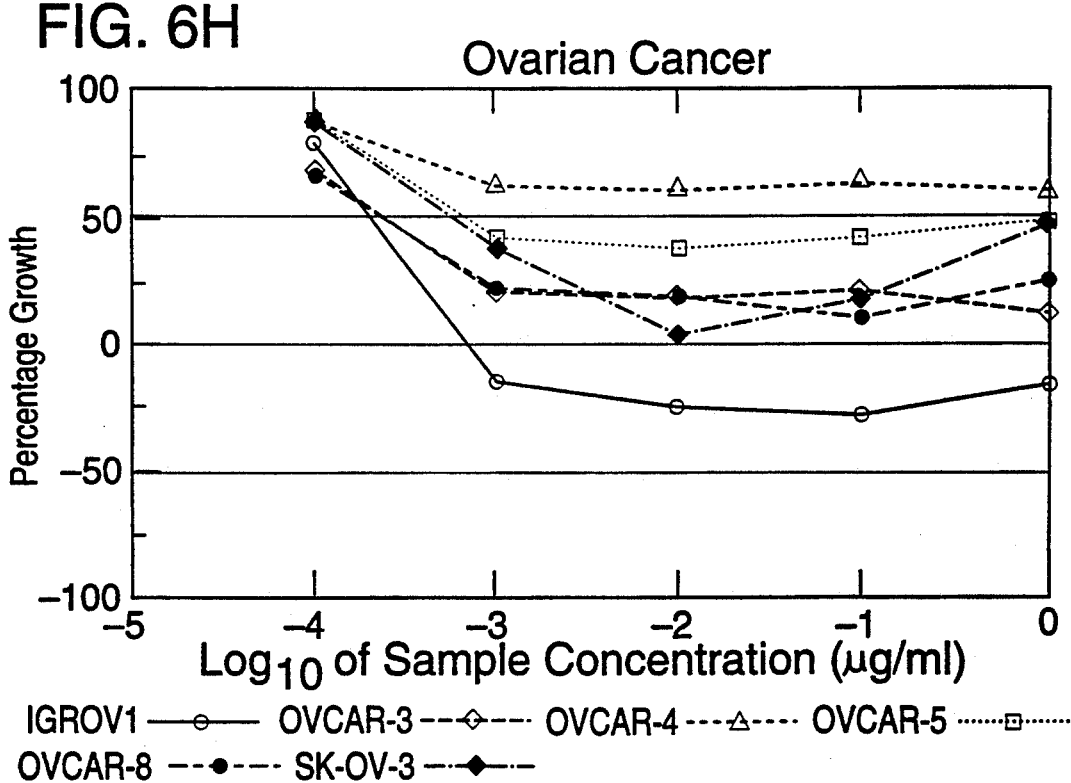

Leukemia

CCRF-CEM —○— K-562 --◇-- MOLT-4 ---▲--- RPMI-8226 ······□······

CNS Cancer

SF-268 —○— SF-295 --◇-- SF-539 ---△--- SNB-19 ······□······
SNB-75 --●-- U251 --◆--

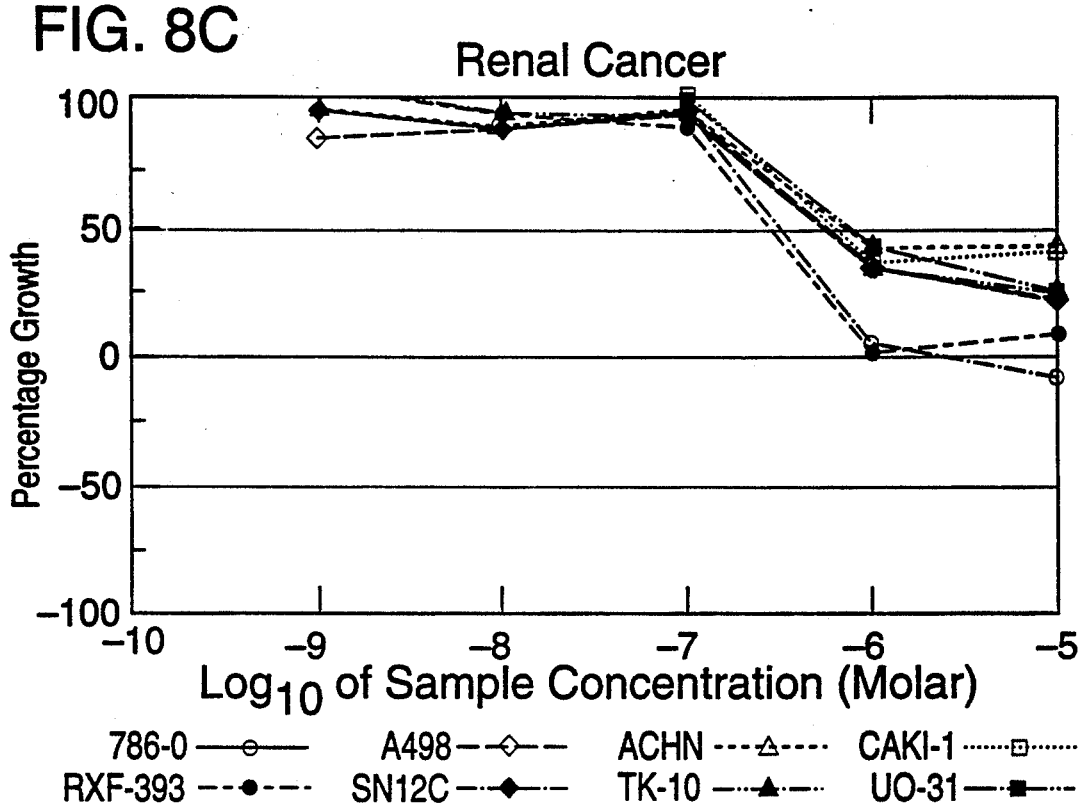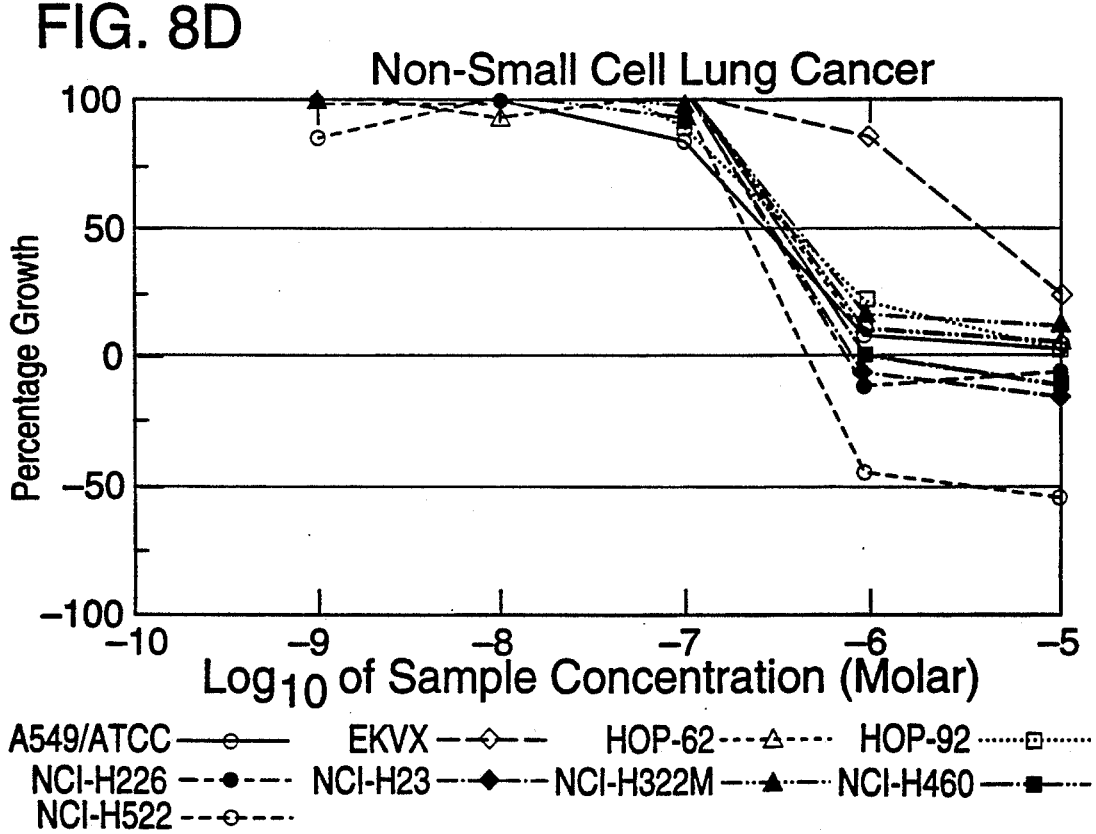

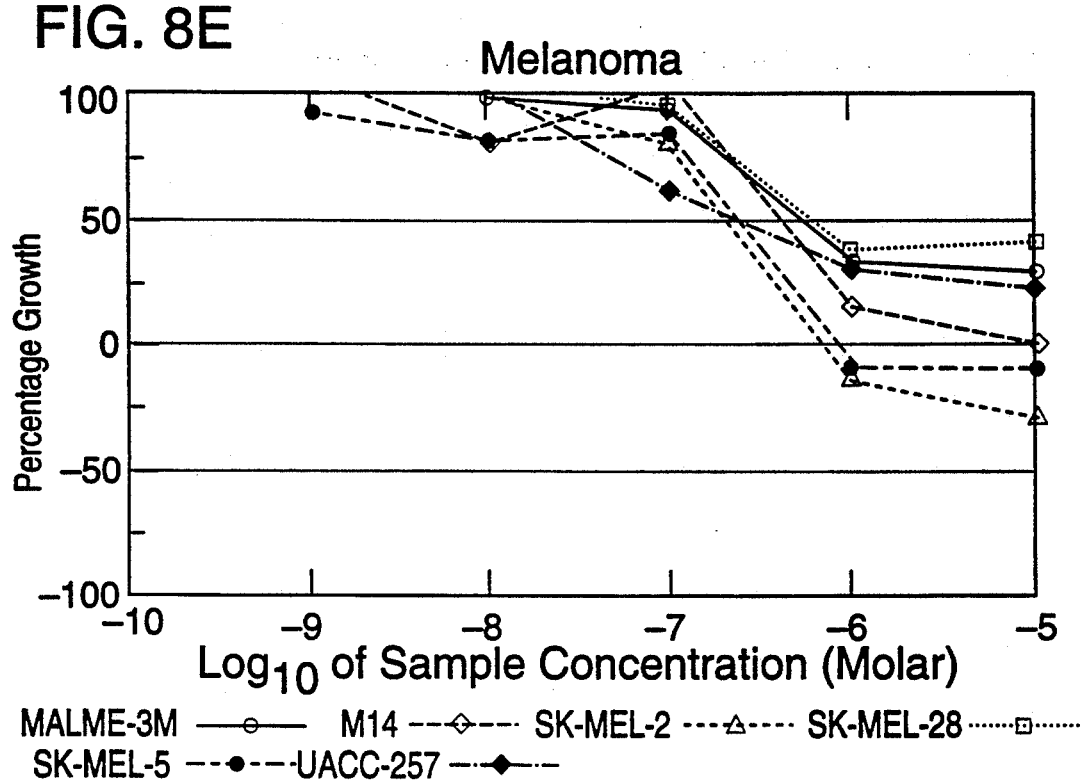
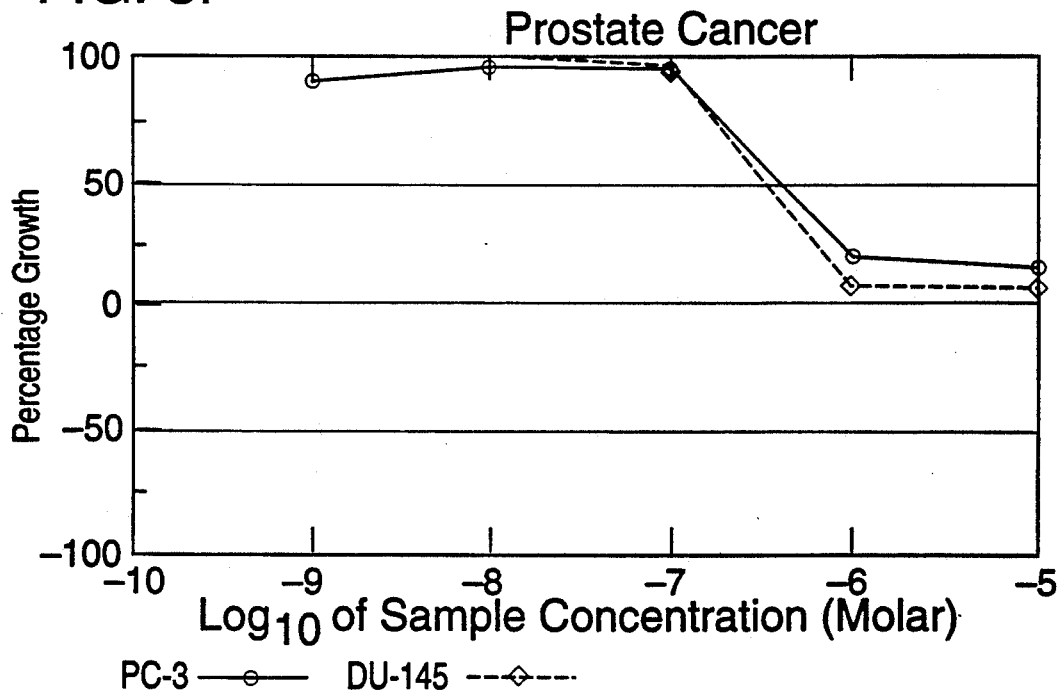

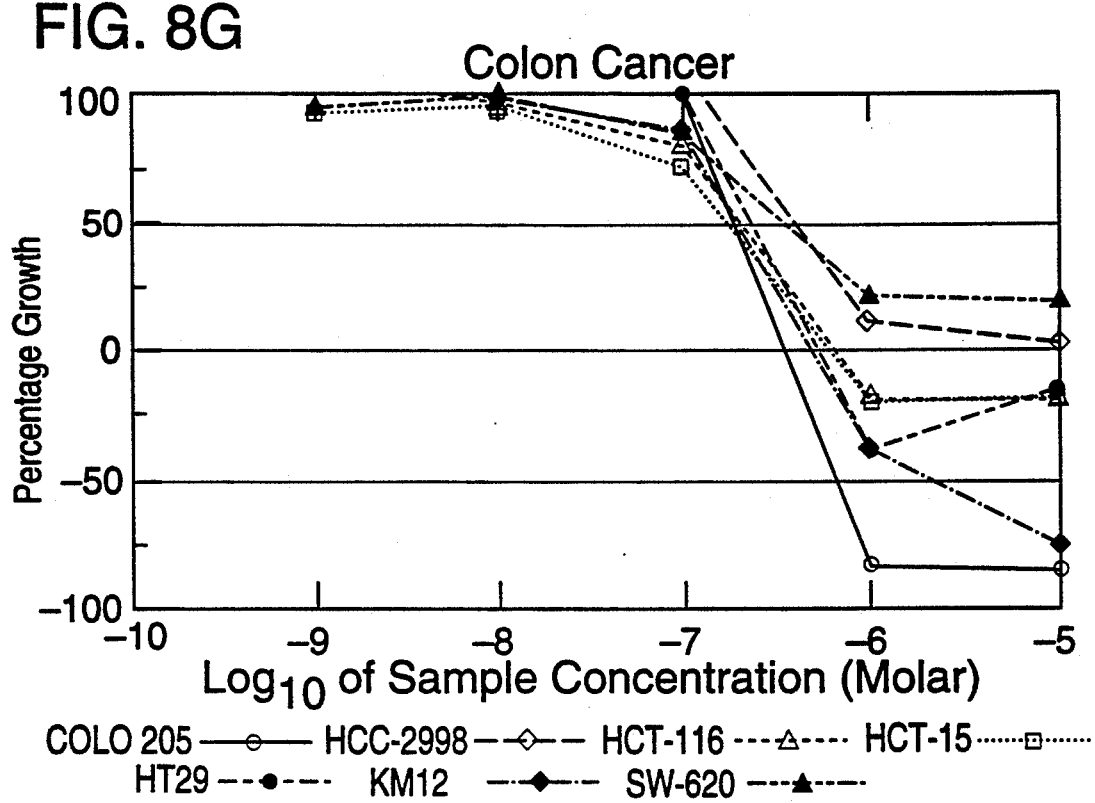
FIG. 8G Colon Cancer
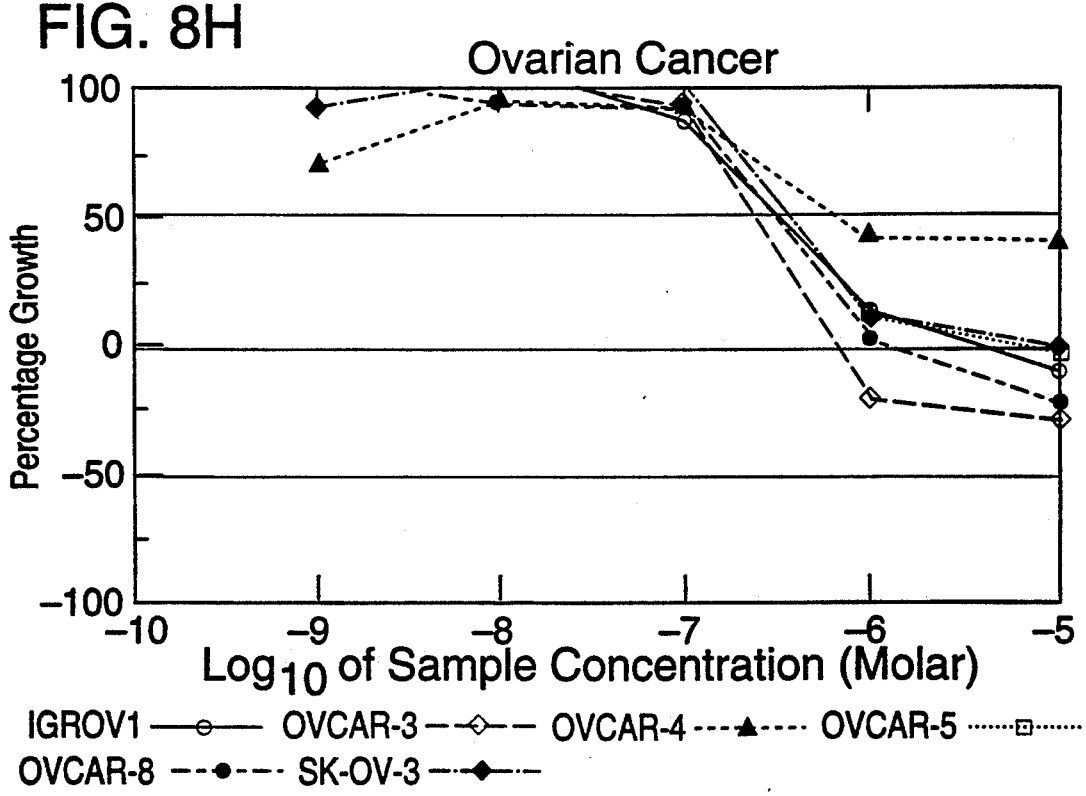
FIG. 8H Ovarian Cancer

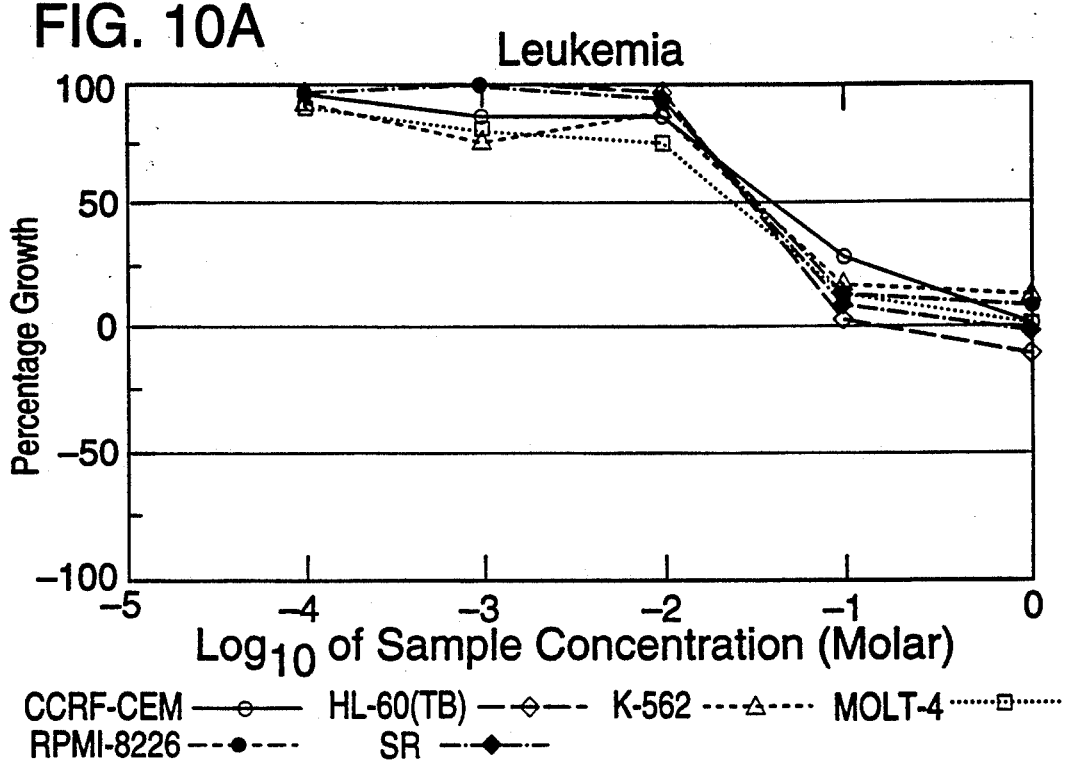
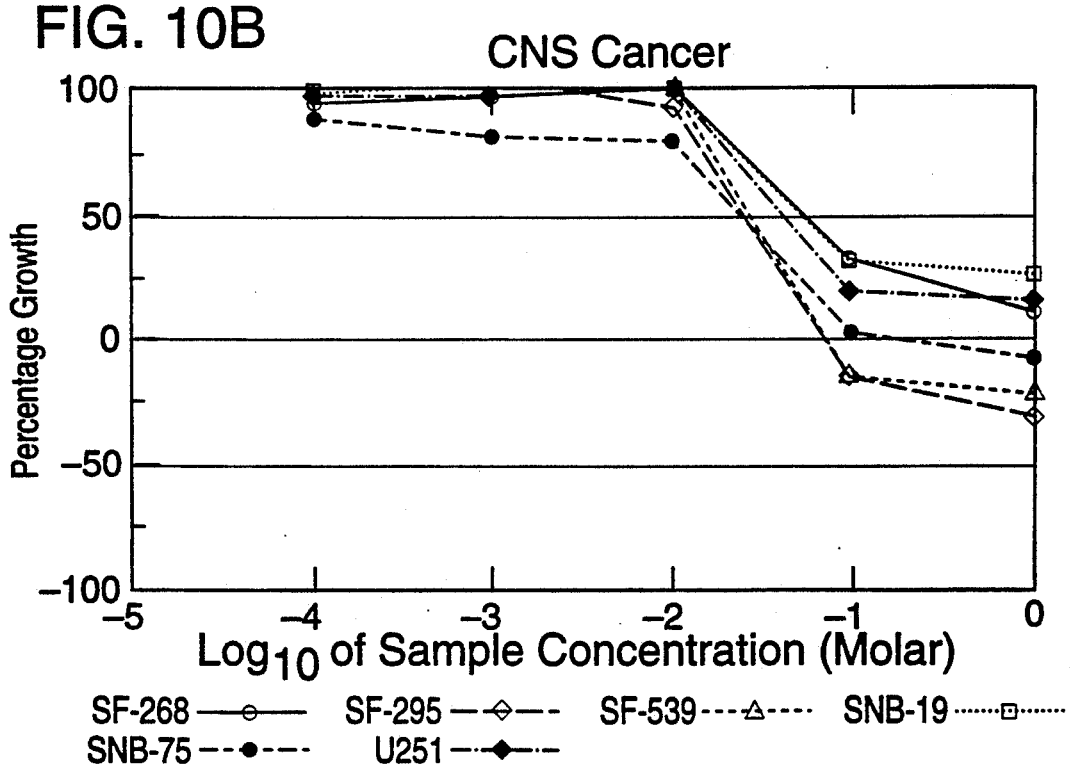

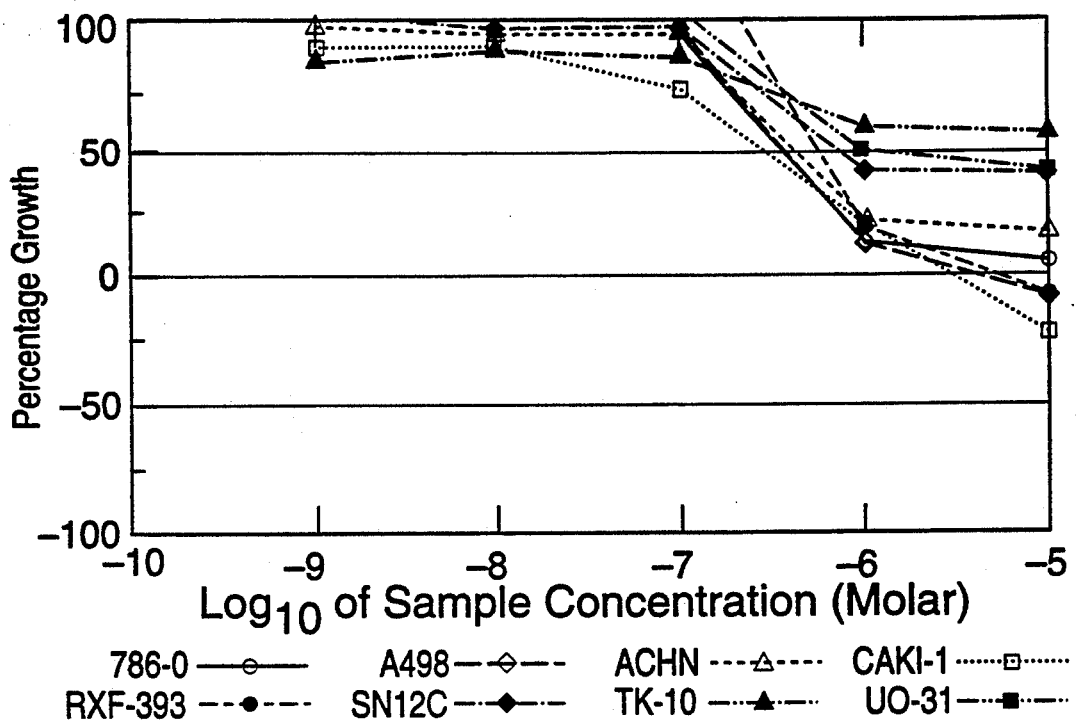
FIG. 10C Renal Cancer
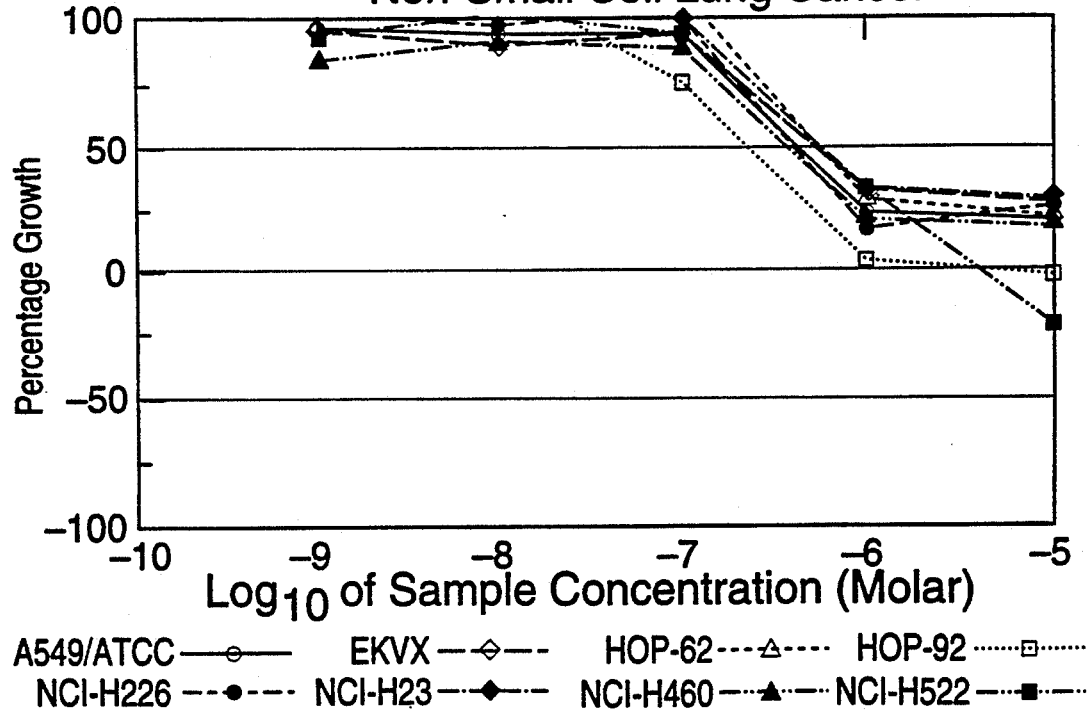
FIG. 10D Non-Small Cell Lung Cancer

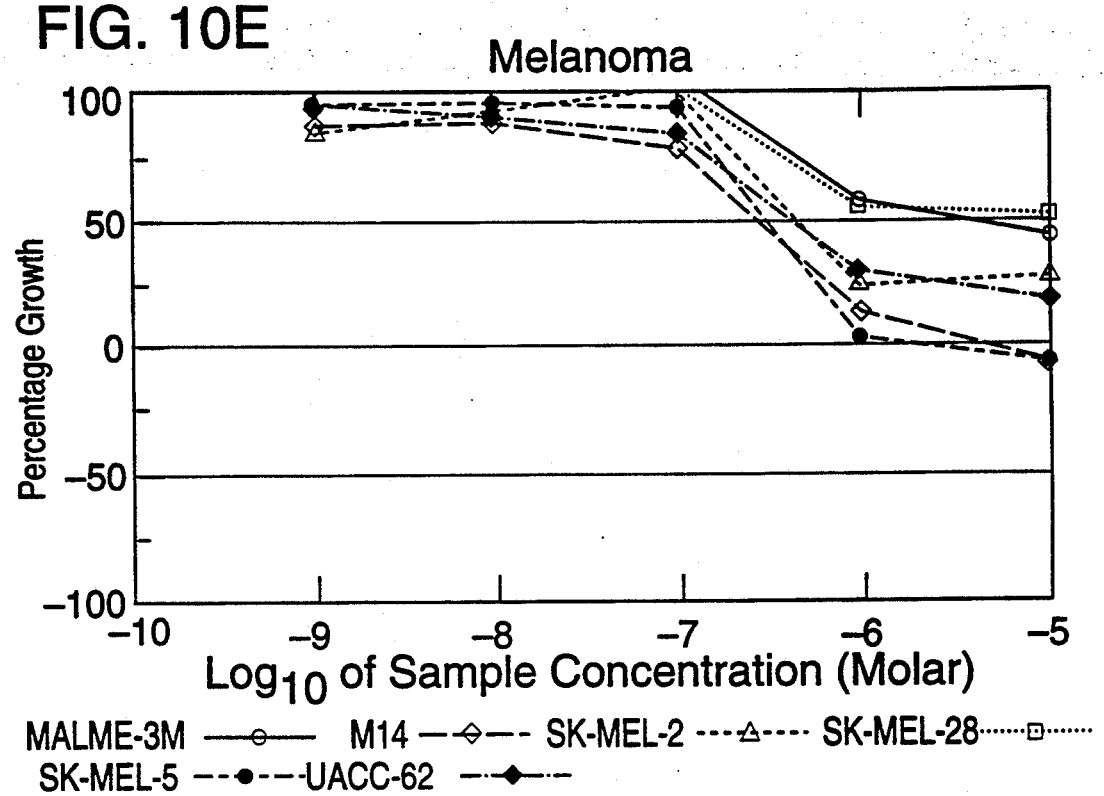
FIG. 10E Melanoma
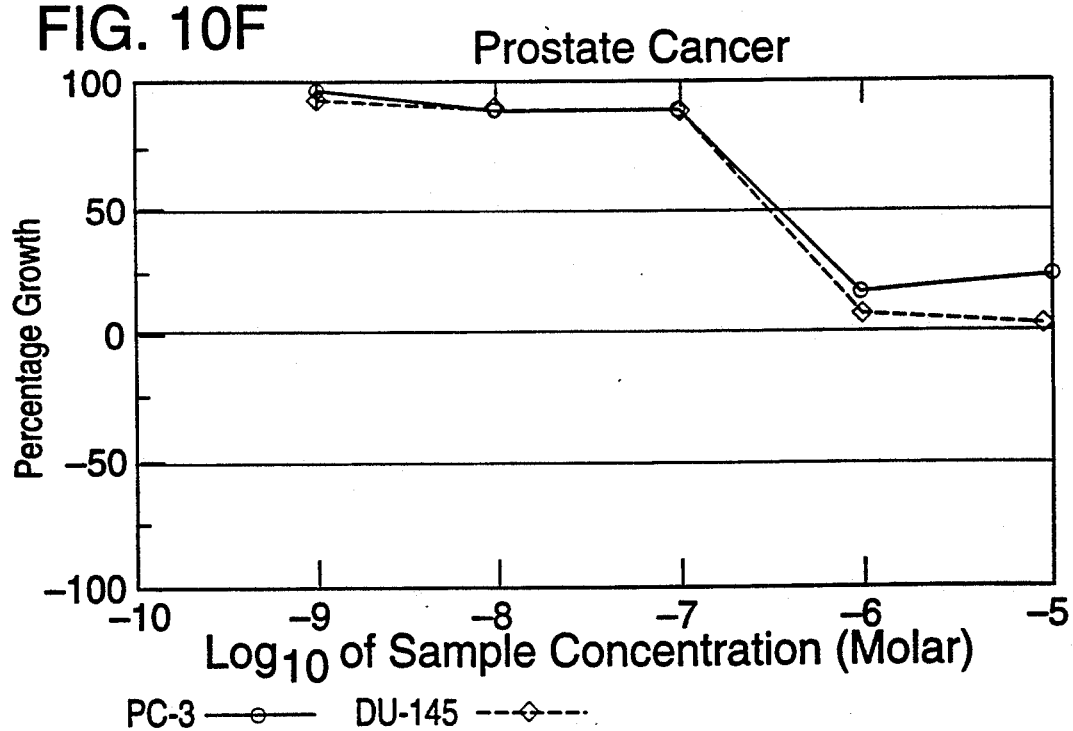
FIG. 10F Prostate Cancer

FIG. 10G Colon Cancer

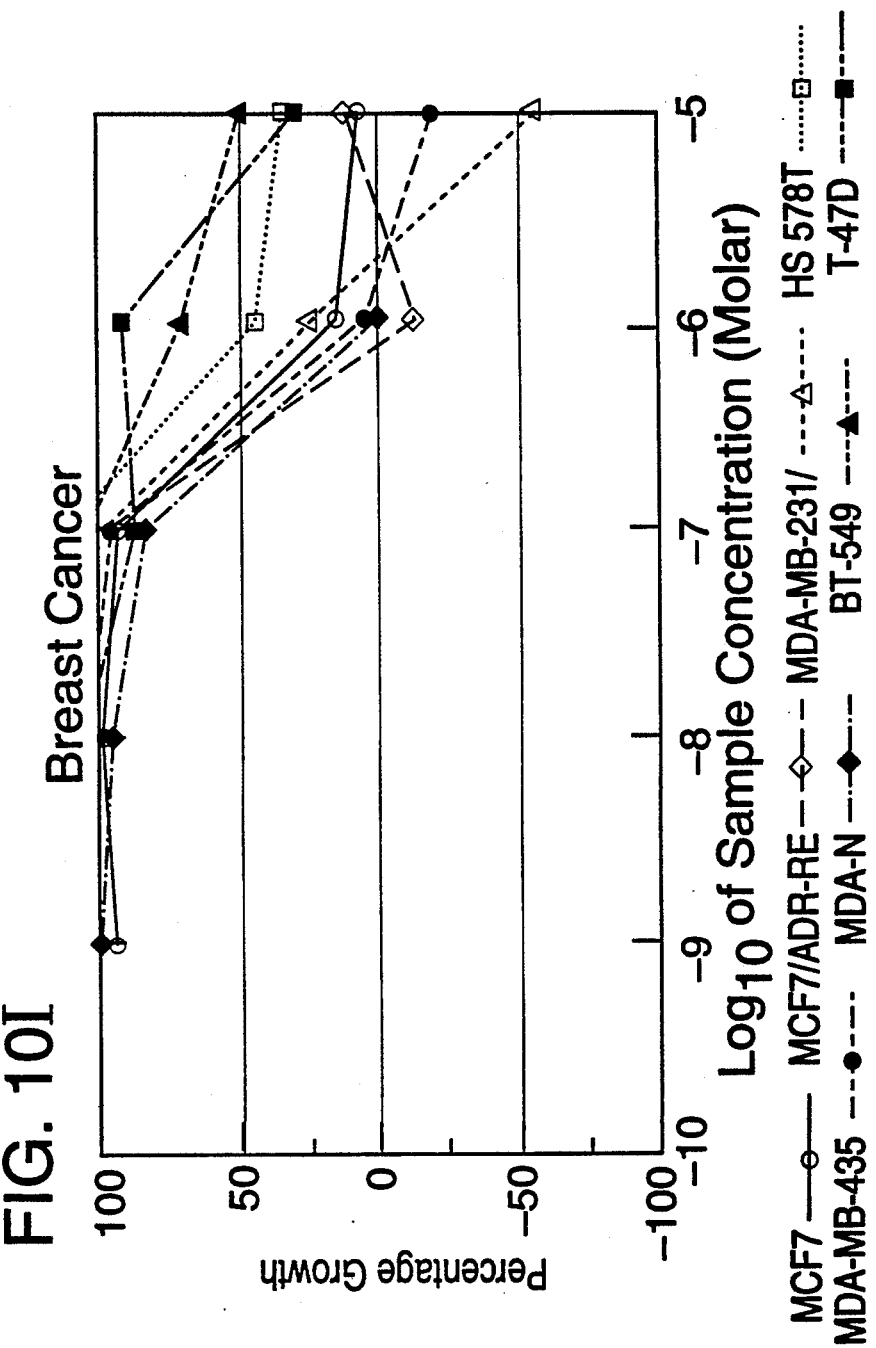

2

COMPOUND EXHIBITING ANTIPROLIFERATIVE ACTIVITY AGAINST CELLS

Work leading to this invention was supported by grant no. CA52955 from the National Institutes of Health. The government has certain rights in this invention.

FIELD OF THE INVENTION

This invention relates to chemical compounds, isolated and purified from a marine blue-green alga (cyanobacterium), exhibiting biological activity.

BACKGROUND OF THE INVENTION

Certain natural environments continue to be fruitful sources of chemical compounds having unusual and unexpected properties, including possible medicinal properties.

In most areas of the world characterized by large species diversity, many plants and animals engage in fierce competition for living space and resource allotment. Certain organisms tend to exhibit unusually high competitive success in such environments. The reasons for such success are several and diverse. Highly successful plants, for example, may produce one or more distinctive chemical compounds that are toxic to nibblers and browsers or that ward off encroaching competitors for living space. Alternatively, there may be other reasons for adaptive success such as a growth rate that is higher than that of competitors, more prolific or efficient reproduction, better drought tolerance, or other characteristic that provides a competitive advantage. In any event, organisms exhibiting competitive success can offer interesting prospects for finding novel chemical compounds having potentially valuable utility in human industry and in medicine.

Blue-green algae (cyanobacteria) have received considerable attention as a source of novel biologically active chemicals. Carter et al., *J. Org. Chem.* 49:236-244 (1984); Moore et al., *J. Am. Chem. Soc.* 106:6456-6457 (1984); Barchi et al., *J. Am. Chem. Soc.* 106:8193-8197 (1984); and Cragg et al., *Am. Soc. Pharmacog. Proceedings*, abst. no. 185 (1985). In the first of the foregoing cited references, Carter et al. reported an abundance of unique secondary metabolites from the principal mat-forming marine cyanobacterium *Lyngbya majuscula* (also named *Microcoleus lyngbyaceus*).

SUMMARY OF THE INVENTION

It has been found that *Lyngbya majuscula* yields several isomers of a cytotoxic compound. One isomer, termed "Curacin A" has the following chemical structure:

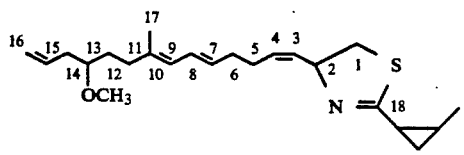

These compounds exhibit substantial activity particularly against proliferating cells and, based upon data obtained during testing against many different types of cultured cancer cells, are believed to function as antimitotic agents.

BRIEF DESCRIPTION OF THE DRAWINGS

FIGS. 6A-6I are dose-response curves showing the effect of the unpurified extract on various cancer cell lines in culture, as set forth in Examples 2-61.

FIGS. 8A-8I are dose-response curves showing the effect of purified Curacin A on various cancer cell lines in culture, as set forth in Examples 62-121.

FIGS. 10A-10I are further dose-response curves showing the effect of purified Curacin A on various cancer cell lines in culture, as set forth in Examples 122-181.

DETAILED DESCRIPTION

A marine blue-green alga (cyanobacterium), *Lyngbya majuscula*, was collected from Carmabi, Curacao (Netherlands Antilles) in the Caribbean on Dec. 13, 1991. From this alga, a new compound was isolated and purified. The new compound, termed "Curacin A," exhibited substantial antimitotic activity in various tests. An isomer of Curacin A, termed "Curacin B," was also discovered.

The alga, harvested at a depth of 0.3 m, was preserved in 90-percent isopropyl alcohol and transported to the U.S. In the laboratory, the alga was subjected to two chloroform-methanol extractions to isolate lipophilic compounds and an aqueous methanol extraction to isolate hydrophilic compounds. Each chloroform-methanol extraction was performed by washing algal tissue in 2:1 chloroform:methanol and collecting the supernatant liquid. The aqueous methanol extraction was performed by washing algal tissue in a 75% solution of methanol in water and collecting the supernatant liquid. The chloroform-methanol extract exhibited substantial toxicity in a brine-shrimp assay, with an $LD_{50}$ of about 25 ng/mL. (Further details on the brine-shrimp assay are set forth below in Example 1.) The brine-shrimp assay was used as needed to evaluate the results of procedures used to purify the compound.

Figure 1:
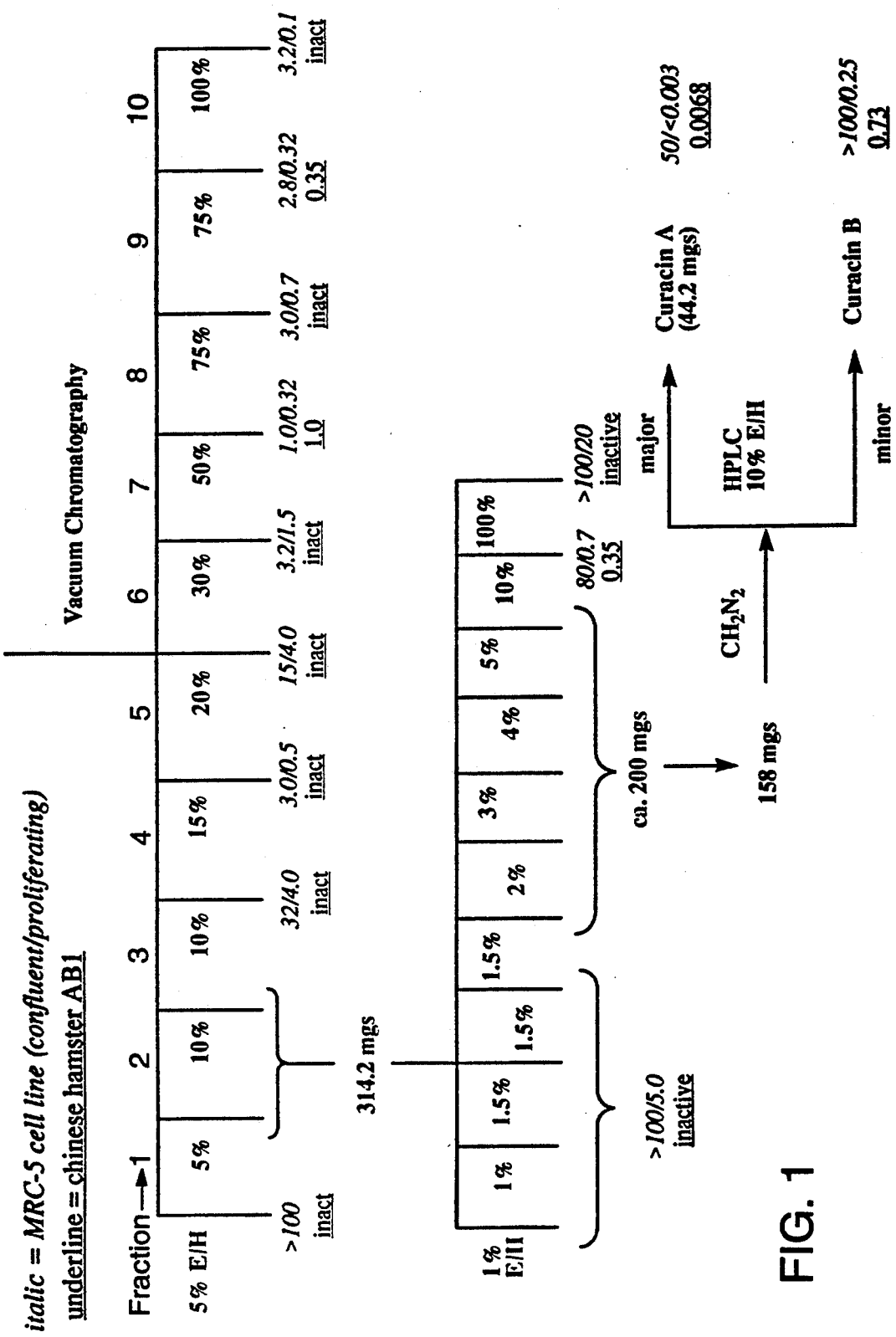
FIG. 1 is a schematic depiction of the general protocol used to purify Curacin A and Curacin B.

For the initial group of studies, the alga were extracted using chloroform-methanol, yielding 2.39 g of "crude" extract. A portion, 543 mg, of the crude extract was subjected to two separate stages of vacuum chromatography as shown in FIG. 1. In the first stage, the extract was eluted using increasingly greater concentrations (5-100% in 5-percent increments) of ethyl acetate in hexane. In the first stage, ten fractions of the eluate were collected. Each fraction was tested for cytotoxicity on cultured MRC-5 cells that were actively dividing, cultured MRC-5 cells that were confluent (and thus not dividing), and actively dividing chinese hamster AB1 tumor cells. The second fraction collected in the first stage, representing elution from 5 to 10% ethyl acetate, had a mass of 314 mg and exhibited the greatest cytotoxicity.

Figure 2:
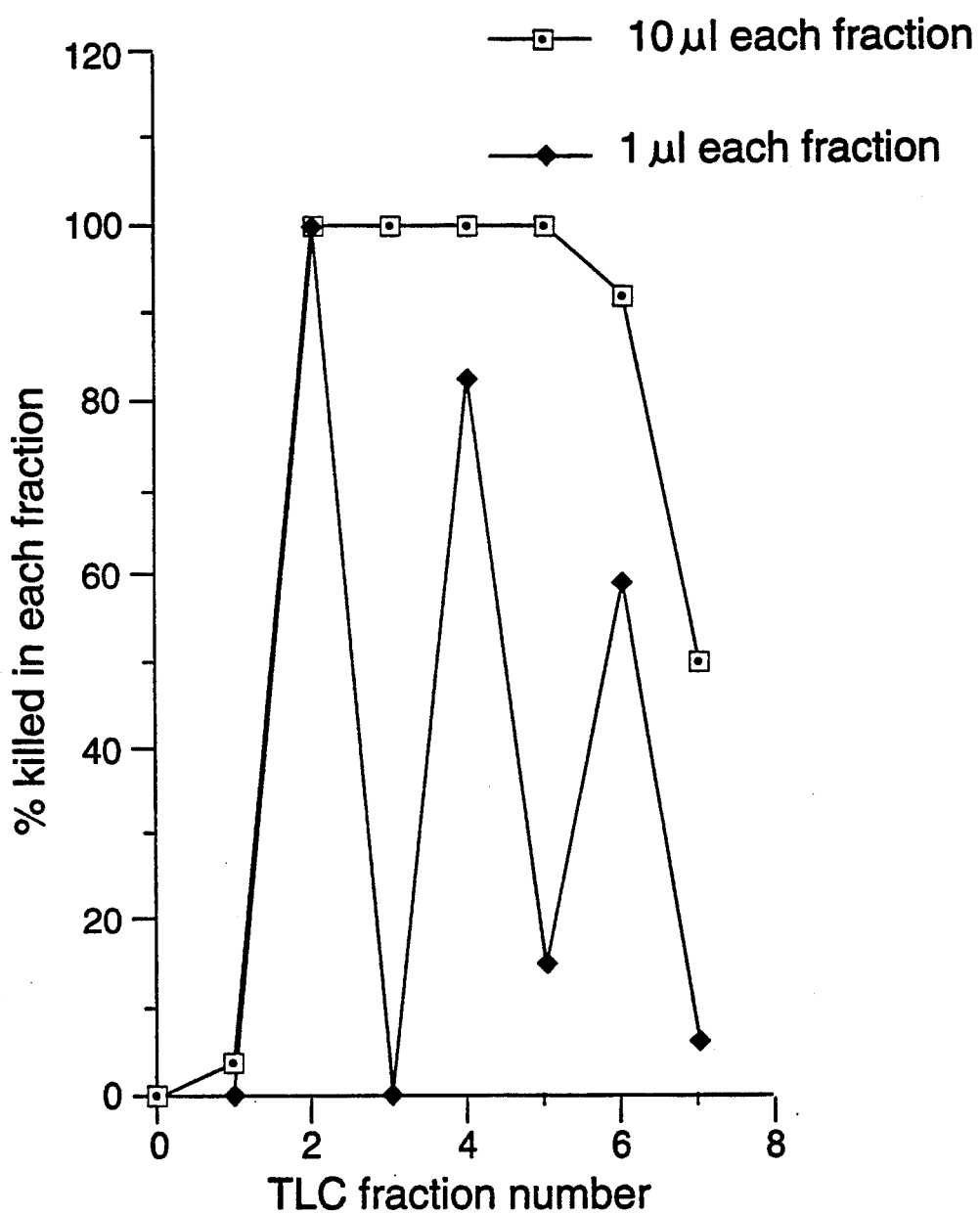
FIG. 2 is a plot of the cytotoxicity of thin-layer-chromatography fractions obtained during purification of these isomers, as determined using a brine shrimp assay.

Thin-layer chromatography confirmed that most of the compound(s) responsible for the activity against brine shrimp was in the second fraction (FIG. 2).

Figure 3:
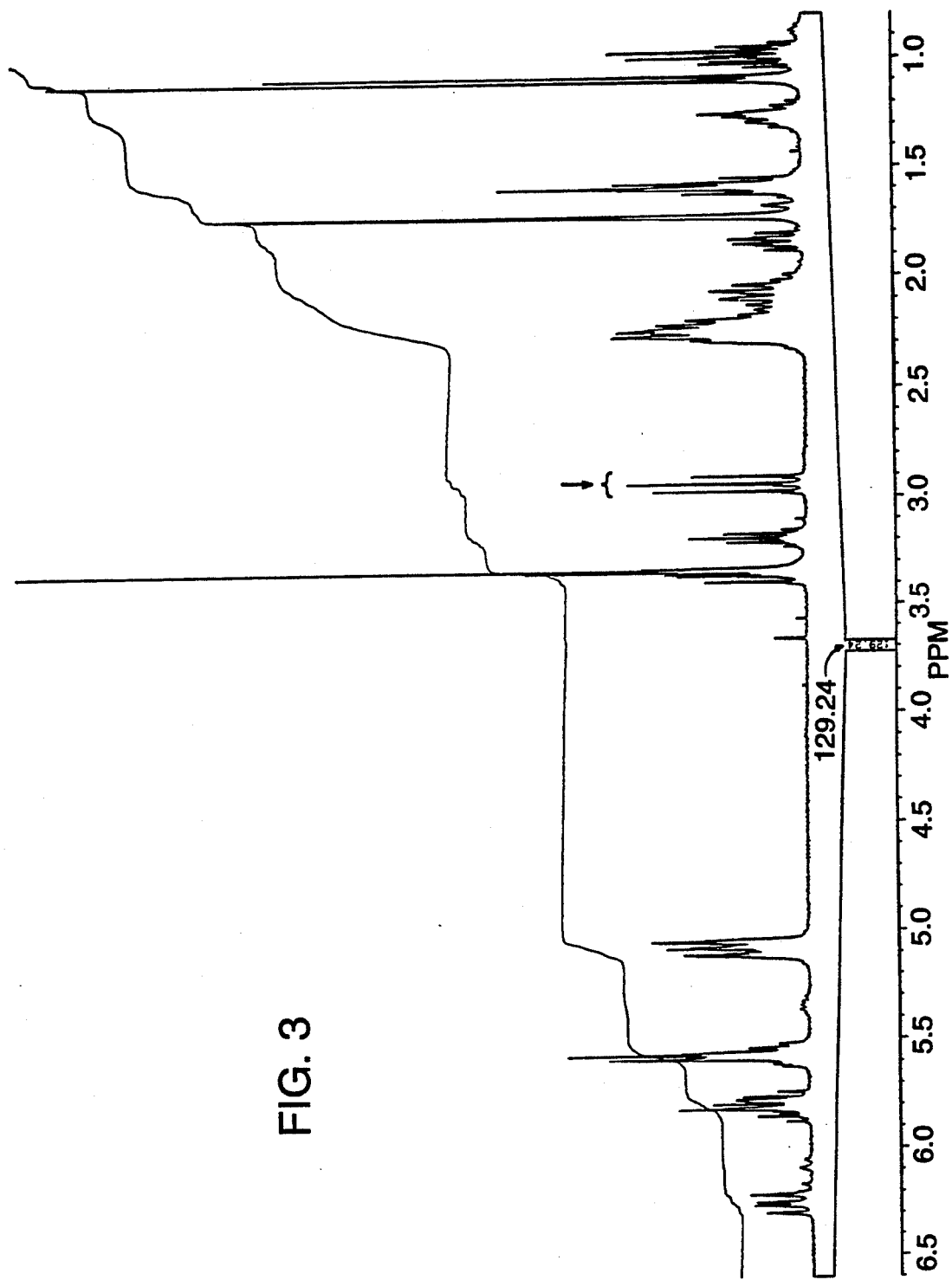
FIG. 3 is a $^1$H-NMR spectrum of a biologically active fraction obtained by vacuum chromatography of an extract from *Lyngbya majuscula*, showing a shouldered triplet indicating that the fraction is a mixture of two isomers, Curacin A and Curacin B.

When analyzed by proton magnetic resonance ($^1$H-NMR) spectroscopy (300 MHz field strength), the second fraction produced a shouldered triplet (arrow, FIG. 3), indicating that these pooled fractions comprised a mixture of two isomers of the active compound. The shoulders were deemed to be due to an isomer, termed "Curacin B," and the corresponding peaks of the triplet were deemed to be due to Curacin A. Curacin A appeared to be present in a greater amount in this fraction than Curacin B.

Referring further to FIG. 1, the second stage of vacuum chromatography was performed on the second fraction collected in the first stage. Elution in the second stage was performed within a much smaller range of increasingly greater amounts of ethyl acetate in hexane (1 to 5% in 0.5 to 1.0% increments). The first four fractions were inactive, but fractions 5-9 showed substantial activity. Fractions 5-9 were pooled and, as such, represented about 200 mg total.

The pooled fractions 5-9 were apparently contaminated by several fatty acids as determined by the following procedures. The mixture was methylated using diazomethane ($CH_2N_2$), to which the Curacin A and Curacin B compounds were found to be unreactive (as further confirmed by $^1$H-NMR). GC-MS (gas chromatography-mass spectrometry) analysis of the methylated mixture revealed that the active compound was present as a mixture with the methylated fatty acids methyl hexadecanoate, methyl-9-octadecenoate, and methyl 11-hexadecenoate, in about equal amounts.

Since the Curacin A and Curacin B compounds were unreactive to $CH_2N_2$, methylation offered a way to purify the compound from the contaminants in the extract. After reaction of the extract with $CH_2N_2$, the extract was subjected to high performance liquid chromatography (HPLC) in an effort to separate the two isomers. (HPLC was performed using a $2 \times 30$ cm Versapack column filled with 10 μm silica gel.) Using 10% ethyl acetate in hexane as an elution solvent, about 44.2 mg (8.1% yield) of Curacin A was obtained as a major fraction free of the fatty acids and substantially free of Curacin B. The Curacin B isomer was present in a minor fraction. As can be seen in FIG. 1, Curacin A was about $10^2$ more active than Curacin B.

The foregoing testing of vacuum chromatography fractions using AB1 cells was performed according to the following protocol: 0.3 mL of cell stock (about $2 \times 10^5$ cells per mL) was added to 2.7 mL of cell culture medium either containing a sample of the fraction or an equal volume of an ethanol control. 100 μL aliquots of the cell suspension were plated into eight wells in each of three 96-well MICROTITER (Dynatech Laboratories, Inc.) plates. The plates were incubated in a tissue culture incubator at 37° C. and 5% $CO_2$. At selected time points (24, 48, and 72 hours), one plate was removed from the incubator and 10 μL of MTT (3-[4,5-dimethylthiazol-2-yl]-2,5-diphenyl tetrazolium bromide) at a stock concentration of 5 mg/mL in phosphate-buffered saline (PBS), was added to each well. The plates were then returned to the incubator for three hours. (In living cells, the activity of mitochondrial enzymes causes the formation of formazen crystals.) Any formazen crystals that formed were solubilized in 0.04M HCl in isopropanol (150 μL per well) added using an eight-channel pipettor. The plates were then "read" using a microplate reader (Molecular Devices), tested at 570 nm, and again at a reference wavelength of 650 nm. Inhibitory concentration values were determined by plotting the percent of control on the third day at various concentrations of the fraction. The 50-percent inhibitory concentration ($IC_{50}$ value) was determined by extrapolation.

Evaluation of the antiproliferative activity of fractions using MRC-5 cells in culture was performed using the following procedure: Human embryonic lung (MRC-5) cells were obtained from the American Type Culture Collection. The cells were grown in Eagle's Minimum Essential Medium with Earle's salts (EMEM, JRH Bioscience) supplemented with 10% fetal calf serum (Hyclone), 0.75 mg/mL $NaHCO_3$, 100 units of penicillin per mL, and 100 μg streptomycin per mL (Gibco Labs). As in the AB1 cell assay, cell growth and survival was determined calorimetrically, based upon the uptake and reduction of the tetrazolium salt, MTT, to a blue-colored formazan product by mitochondrial enzymes of living cells. The effect of the fractions, as potential inhibitors at different stages of the cell cycle, was determined by performing the assay using both resting and rapidly dividing cells. Plates exhibiting either confluent cells (resting phase) or proliferating cells (rapidly dividing phase) were incubated with various concentrations of the extracts for four days at 37° C. in air containing 5% $CO_2$. At the end of the incubation, the medium was aspirated, the cells were rinsed once using PBS, and 1.0 mg/mL of MTT was added to each well. The plates were incubated with MTT for three hours, after which the MTT was aspirated and isopropanol was added to dissolve any formazen crystals that formed. Plates were "read" on an Elisa reader at 570 nm (principal wavelength) and again at 650 wavelength (reference wavelength) to correct for non-specific background absorbance, using a Thermomax Spectrophotometer (Molecular Devices). The inhibitory concentration of extract that reduced cell viability by 50% (IC50) when compared to controls was estimated using a non-linear regression modeling software program.

Figure 4:
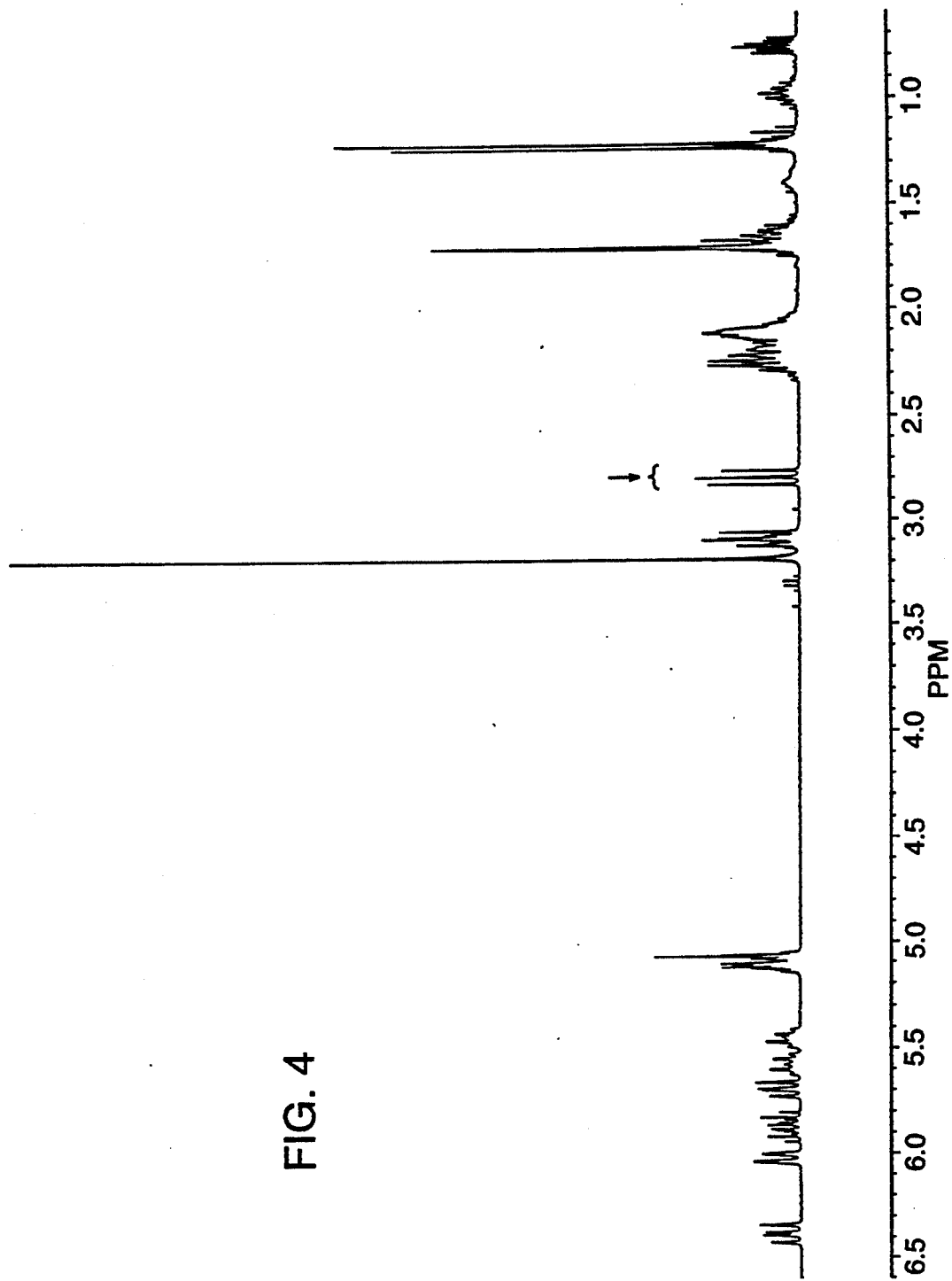
FIG. 4 is a $^1$H-NMR spectrum of the fraction of FIG. 3 after purification via HPLC so as to separate the isomers.

The major fraction containing Curacin A was evaluated by $^1$H-NMR (300 MHz field strength) and the results are shown in FIG. 4. Comparing FIG. 4 with FIG. 3, it can be seen that the shoulders on the triplet discussed above are missing in FIG. 4 (arrow), indicating that the major fraction containing Curacin A is substantially free of the isomer Curacin B.

High-resolution Fast-Atom-Bombardment mass spectrometry (FAB-MS; positive ion, 3-nitrobenzyl alcohol) was performed on the Curacin A-containing major fraction, which exhibited a major $[M+H]^+$ ion at m/z 374.2520 analyzing for $C_{23}H_{36}ONS$ (0.3 milli-atomic mass units deviation from the predicted molecular weight). Hence, Curacin A, having the empirical formula $C_{23}H_{35}ONS$, possessed seven degrees of unsaturation, five of which were due to double bonds and two due to rings.

Using the foregoing, Curacin A was determined to have the structural formula as shown below:

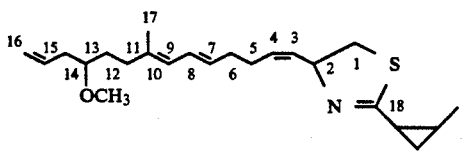

The Curacin B isomer present in the minor fraction is believed to be a stereoisomer of Curacin A, probably at C2, or possibly the double-bond geometry at C3–C4.

Data from $^1H$-$^1H$ COSY (correlation spectroscopy) and $^1H$-$^{13}C$-HETCOR (heteronuclear chemical shift correlation) were used to ascertain the structure for the left-hand portion of Curacin A. The left-hand portion began with a monosubstituted terminal olefin that was adjacent to a methylene group. Neighboring the methylene group was a deshielded methine (C13) that was shown by HMBC (heteronuclear multiple bond correlation) to bear an O-methyl group. Sequential $^1H$-$^1H$ correlations placed two consecutive methylene groups (C11 and C12) contiguous to the deshielded methine, the latter methylene group being adjacent to a quaternary carbon.

The middle portion of the Curacin A molecule was found to begin with a terminal methylene group (C1) bearing a heteroatom (the sulfur in the 5-membered ring) adjacent to a methine carbon (C2) also bearing a heteroatom (the nitrogen in the 5-membered ring). The proton adjacent to the nitrogen atom was coupled to an olefinic proton at δ5.69, which in turn coupled by 10.7 Hertz to its olefinic partner. Two methylene groups (C5 and C6) spanned between this olefin (C3 and C4) and a conjugated diene (C7–C10). The first of the olefins (C7 and C8) in the conjugated diene was disubstituted and trans while the second olefin (C9 and C10) was trisubstituted and possessed methyl (C17) and alkyl (C11–C16) substituents at its distal portion (C10). The geometry of the second olefin was shown to be E by the high-field $^{13}C$-NMR chemical shift of the methyl group (C17) at δ16.56.

The structure on the right-hand portion of the molecule was readily formulated, from spin-coupling information, as a cis-disubstituted cyclopropyl ring with methyl and quaternary carbon substituents.

HMBC was used to make further confirmation of structure. The protons alpha to the two heteroatoms in the five-membered ring were both correlated to the quaternary carbon (C18). Similarly, long-range coupling was observed between the olefinic proton at δ6.02 (on C9) and the methylene carbon at δ35.77 (C11). Assigning sulfur as the heteroatom bonded to C1 and nitrogen as the heteroatom bonded to C2 were based on comparisons of $^{13}C$-NMR chemical shifts with model compounds, Hawkins et al., *J. Med. Chem.* 33:1634–1638 (1990); and Jalal et al., *J. Am. Chem. Soc.* 111:292–296 (1989), thereby defining a thiazoline ring. Thus, Curacin A was found to be a substantially planar molecule having a cyclopropyl ring and long-chain alkene substituents.

Curacin A appears to be different from any other known chemical. The alkylated thiazoline portion of the molecule is also believed to be unique, but appears to have some similarity to the potent cytotoxins patellazole A-C from the tunicate *Lissoclinum patella*. Zabriskie et al., *J. Am. Chem. Soc.* 10:7919 (1988). I.e., the patallazoles possess four-carbon epoxides and long polyketide chain substituents on a thiazole ring. While the alkyl substituent in the patellazoles is considerably more complex than that in Curacin A, patellazoles and Curacin A both have similar chromophores at about the same location relative to the thiazoline/thiazole rings. Similar substituted diene or triene functionalities are observed in two other well-known antimitotic agents, maytansine and rhizoxin.

From a biosynthetic perspective, it is possible that Curacin A is formed by the union of two polyketides, joined via a decarboxylated cysteine residue.

Based upon comparisons with analogous biologically active portions of other compounds that exhibit biological activity, the biologically active portions of Curacin A are believed to include the cyclopropyl portion, the heterocyclic ring, and the conjugated diene. In any event, Curacin A and Curacin B appear to be readily penetrate cell membranes, probably due to the substantial lipophilicity of these compounds (particularly the long olefinic "tail" extending away from the heterocyclic ring).

Utility

Curacins A and B have been found to be cytotoxic compounds that appear to be antimitotics, probably by interfering with cellular mechanisms of tubulin formation. Tests performed using nearly sixty different cancer cell lines (see Examples below) indicate that the cytotoxic profile of Curacin A and its stereoisomers shares certain similarities with other antimitotic agents, such as the Vinca alkaloids and taxol, that are useful as antineoplastics. Thus, it would be within the purview of persons skilled in the art of preparing pharmaceutical formulations to add Curacin A (and/or a stereoisomer thereof) to a pharmaceutically inert carrier suitable for administration to an animal subject, in a manner similar to that used for preparing such formulations of conventional antimitotic compounds.

The effectiveness of Curacin A and stereoisomers thereof for reducing a population of representative arthropods (brine shrimp; see Example 1) indicate that the Curacin A and Curacin B compounds have general utility as agents for reducing populations of arthropods such as insects.

The Examples set forth below also indicate that Curacin A, and stereoisomers thereof, has substantial antiproliferative activity against living cells in culture.

Tests involving administration of formulations containing Curacins A and B to mice (data not shown) indicate that the Curacins A and B are bioavailable and effective in vivo against proliferating cells when administered by various direct methods and when administered orally. These results are consistent with similar attributes of conventional antimitotic agents. In addition, these tests indicate that Curacins A and B can be administered to animal subjects using dosage protocols that are substantially similar to such protocols used with other antimitotics.

Ex vivo experiments involving the administration of formulations containing Curacins A and B to mice (1–10 mg/kg) indicate that Curacins A and B exhibit substantial effect against spleen lymphocytes, and may have general utility as an immunosuppressive or antiinflammatory agent.

The results and data set forth in this disclosure indicate that the Curacins A and B are more active against proliferating cells than against quiescent cells.

Consistent with the herbicidal activity of conventional antimitotic compounds, the Curacins A and B would be expected to also exhibit herbicidal properties.

EXAMPLE 1

In this Example, various concentrations of the organic extract of Lyngbya majuscula were tested using a brine-shrimp assay. The assay was performed according to the following procedure: 24 hours before performing the assay, brine shrimp eggs were hatched in sea water (made by dissolving INSTANT OCEAN dry concentrate in water according to manufacturer's directions). A volume of the organic extract of Lyngbya majuscula was placed in a 50-mL conical flask (weighed beforehand to obtain the tare weight) and the solvent was evaporated. The flask was re-weighed and the tare weight subtracted to yield the weight of non-volatile residue from the extract. The residue was dissolved with a suitable volume of ethanol to yield a concentration of 0.1 mg residue per $\mu$L ethanol. Four vials were prepared, the first containing 50 $\mu$L of the ethanol solution, the second containing 10 $\mu$L of the ethanol solution plus 40 $\mu$L ethanol, the third containing 2.5 $\mu$L of the ethanol solution plus 47.5 $\mu$L ethanol, and the fourth containing none of the solution and 50 $\mu$L ethanol (serving as a negative control). Between 10 and 15 live brine shrimp were placed in each vial and stored for 24 hours, after which the number of live and dead shrimp were tallied for each vial. For each vial, the number of dead shrimp was divided by the total number of shrimp added to the vial, and multiplied by 100 to yield the percent mortality for each vial. The data are plotted as percent alive versus the $\log_{10}$ of the concentration of extract added to the corresponding vials.

Figure 5:
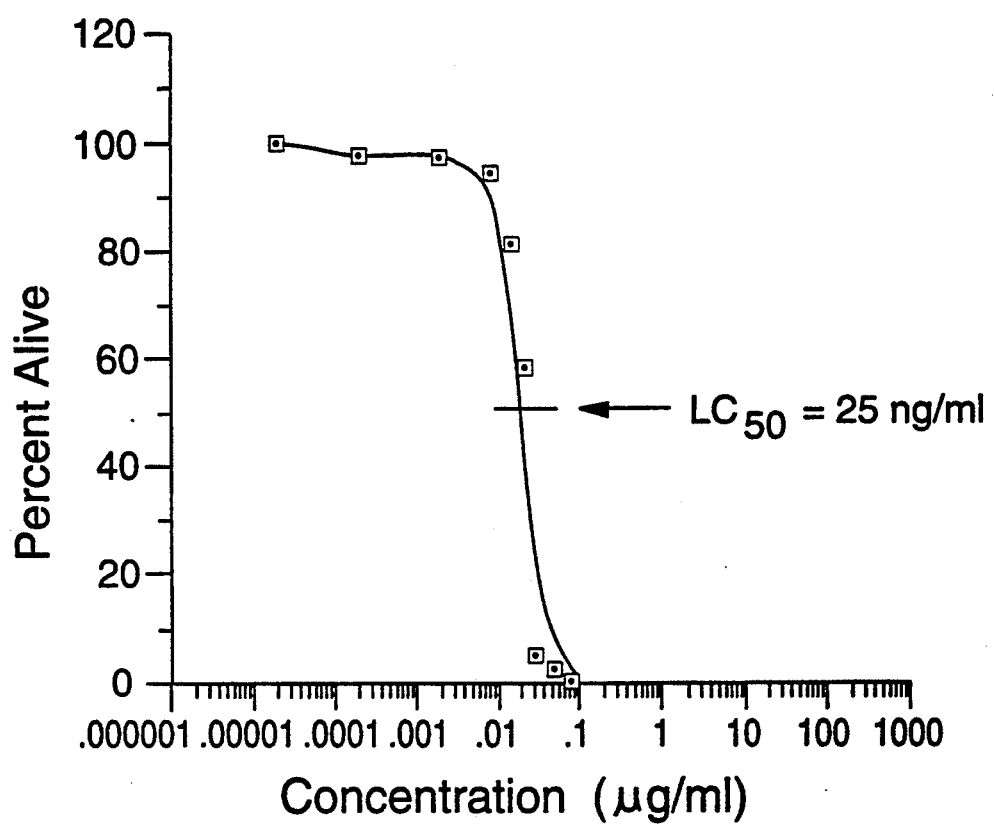
FIG. 5 is a plot of data obtained from a brine shrimp assay performed with the unpurified extract from *Lyngbya majuscula*.
Figure 6A:
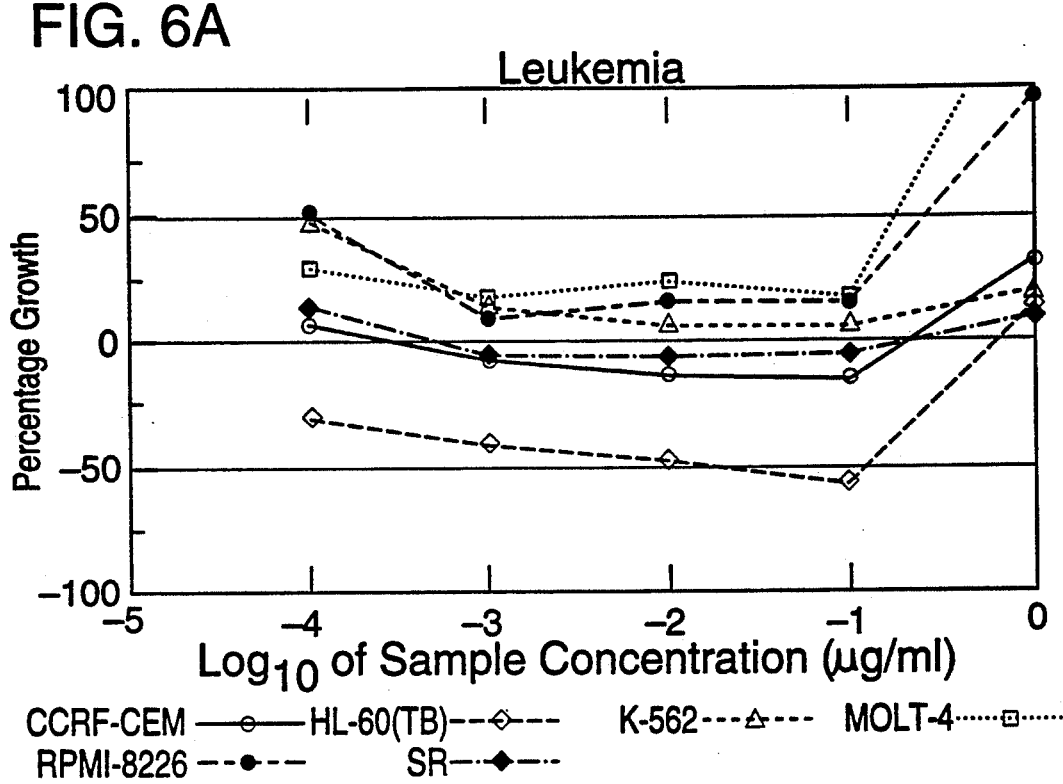
Figure 6B:
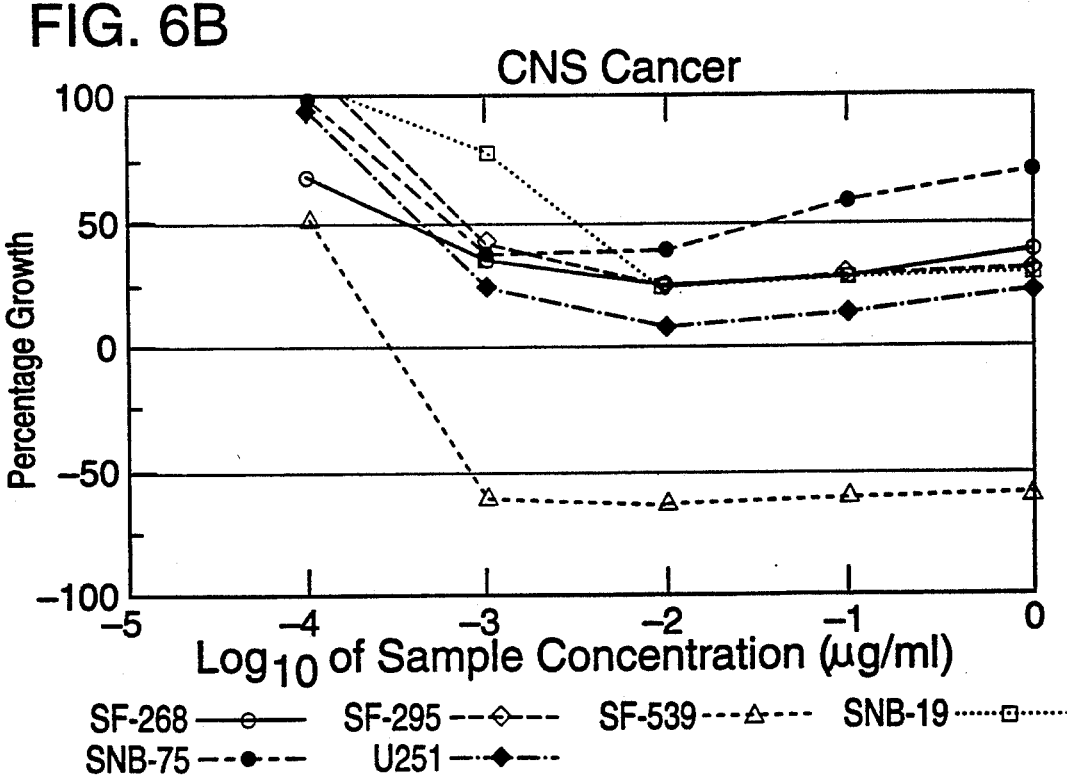
Figure 6E:
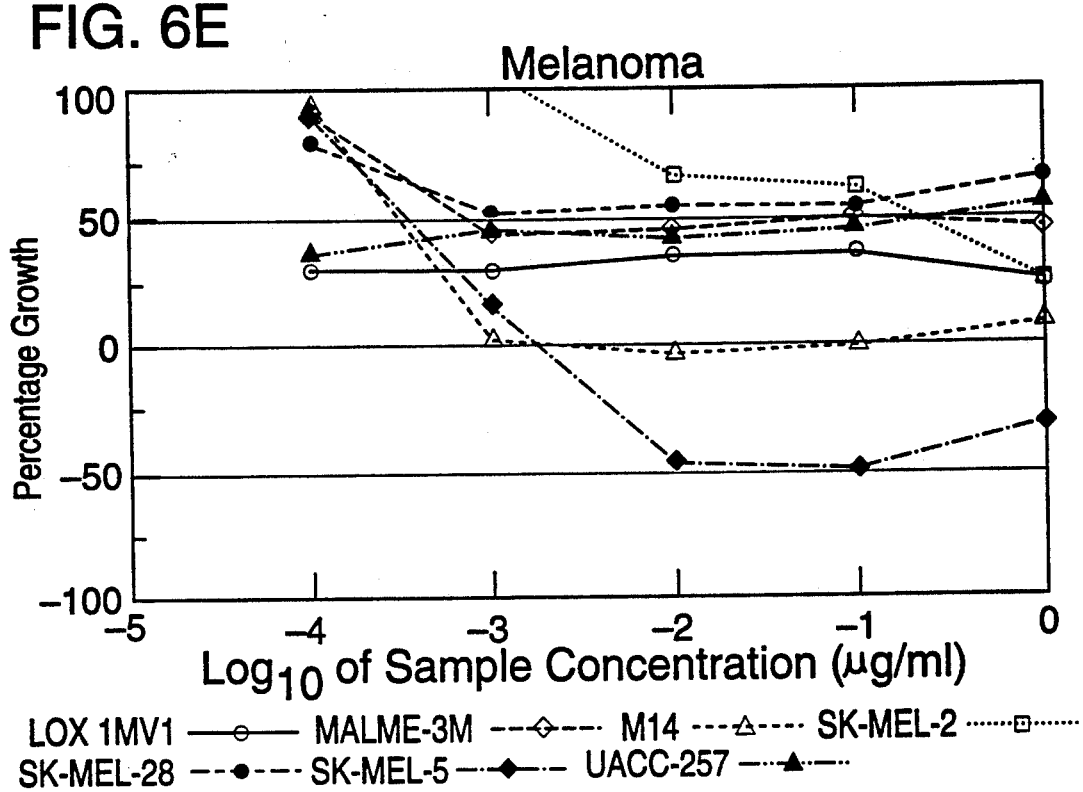
Figure 6F:
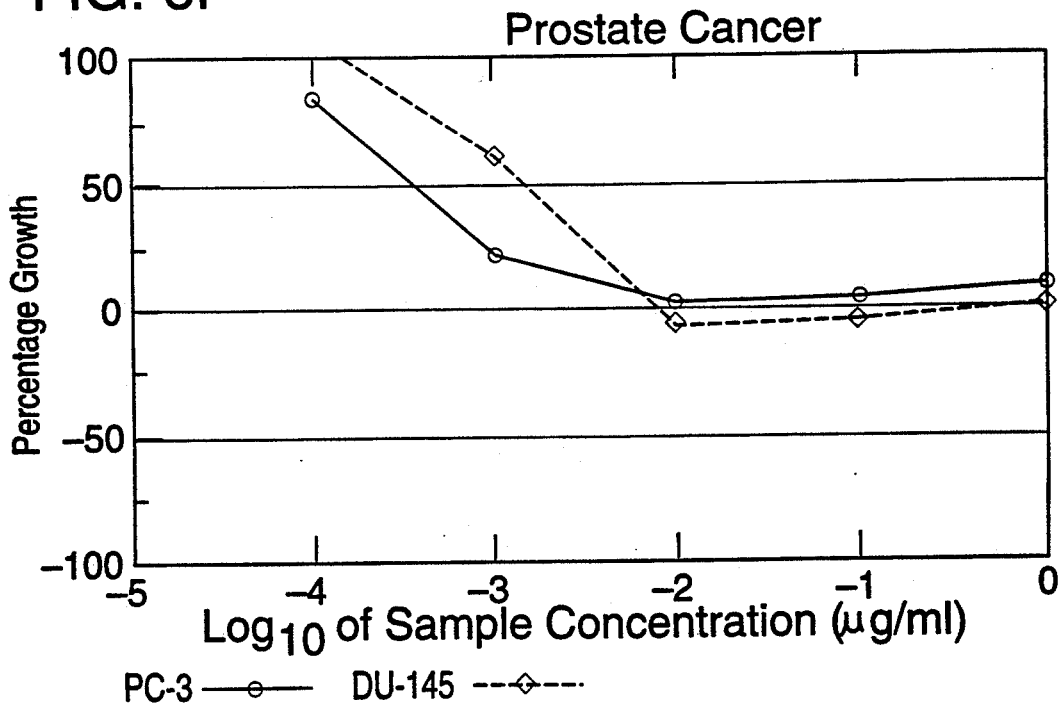
Figure 6I:
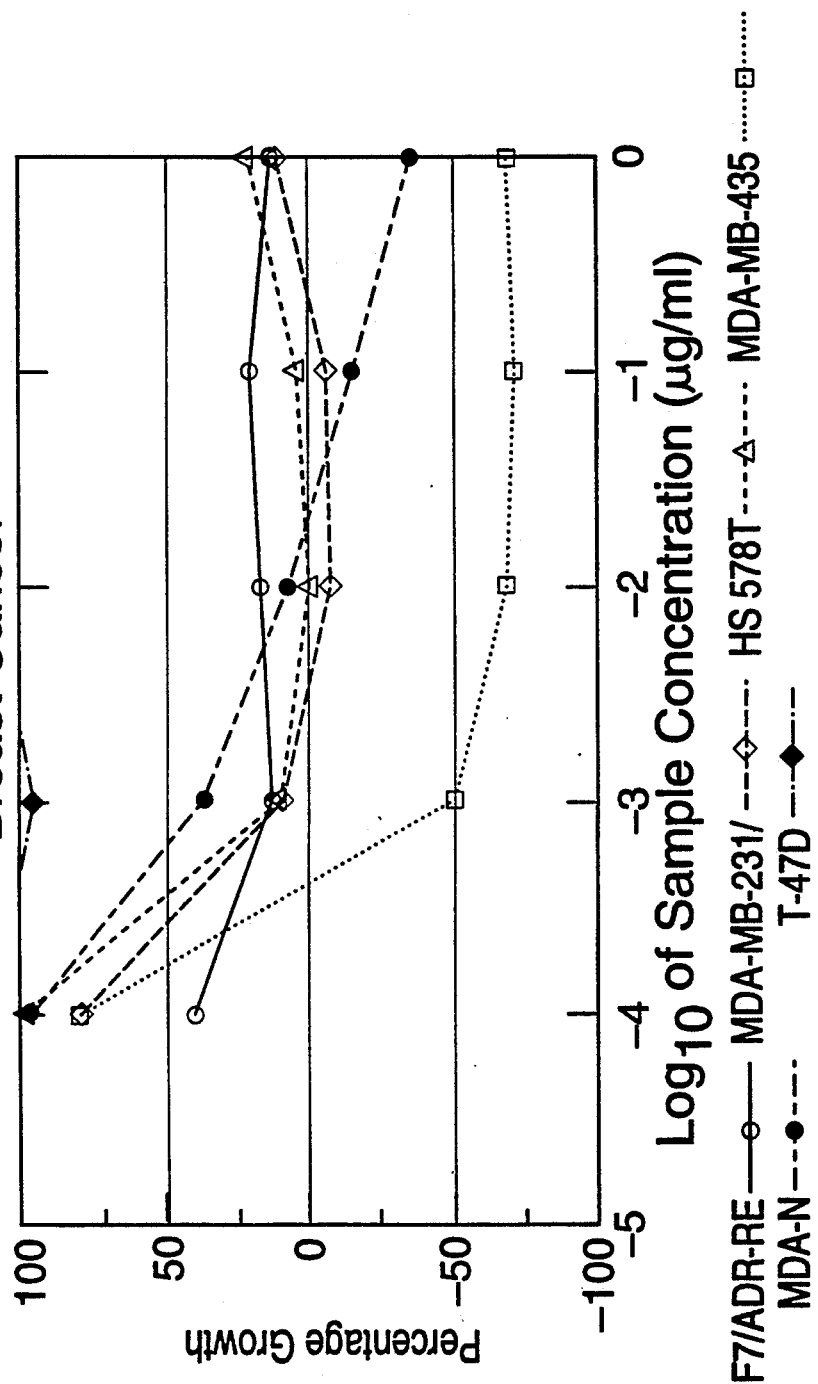

A plot of the data is shown in FIG. 5. The $LC_{50}$ concentration value, about 0.025 $\mu$g/mL, is the concentration of the extract at which 50% of the brine shrimp are killed.

EXAMPLES 2-61

In these examples, an extract of Lyngbya majuscula containing Curacins A and B was subjected to the drug screening procedure employed by the National Cancer Institute for the screening of drugs having possible anticancer utility.

The screening procedure employed a diverse, disease-oriented panel consisting of 60 different human tumor cell lines organized into seven disease-specific subpanels. The extract was tested over a wide range of concentrations for cytotoxic or growth-inhibitory effects against each cell line comprising the panel. The seven subpanels represented diverse histologies (leukemias, melanomas, and tumors of the lung, colon, kidney, ovary, and brain).

The extract was tested over two days in which the cells were continuously exposed to five $\log_{10}$-spaced concentrations of the drug starting at $10^{-4}$ $\mu$g/mL. The tests produced 60 individual dose-response curves, one for each cell line (i.e., one for each example).

The data are disclosed in FIGS. 6A–6I as dose-response curves. The data of FIGS. 6A–6I are summarized using a mean-graph format, as shown in FIG. 7.

Figure 7A:
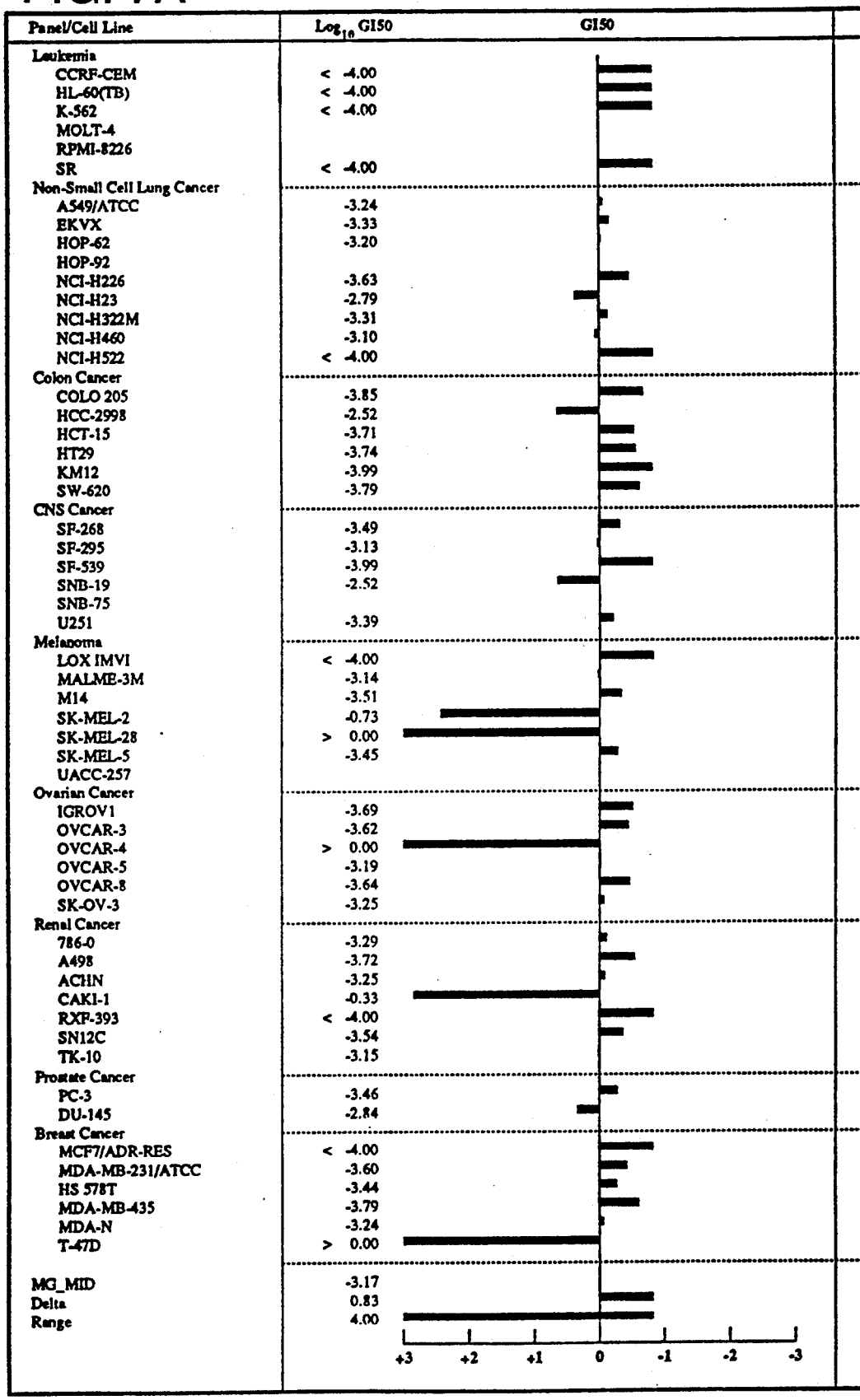
FIGS. 7A-7B show mean-plots of data from FIGS. 6A-6I, wherein the left-hand mean plot is of $GI_{50}$ data, the middle mean plot is of TGI data, and the right-hand mean plot is of $LC_{50}$ data.
Figure 7B:
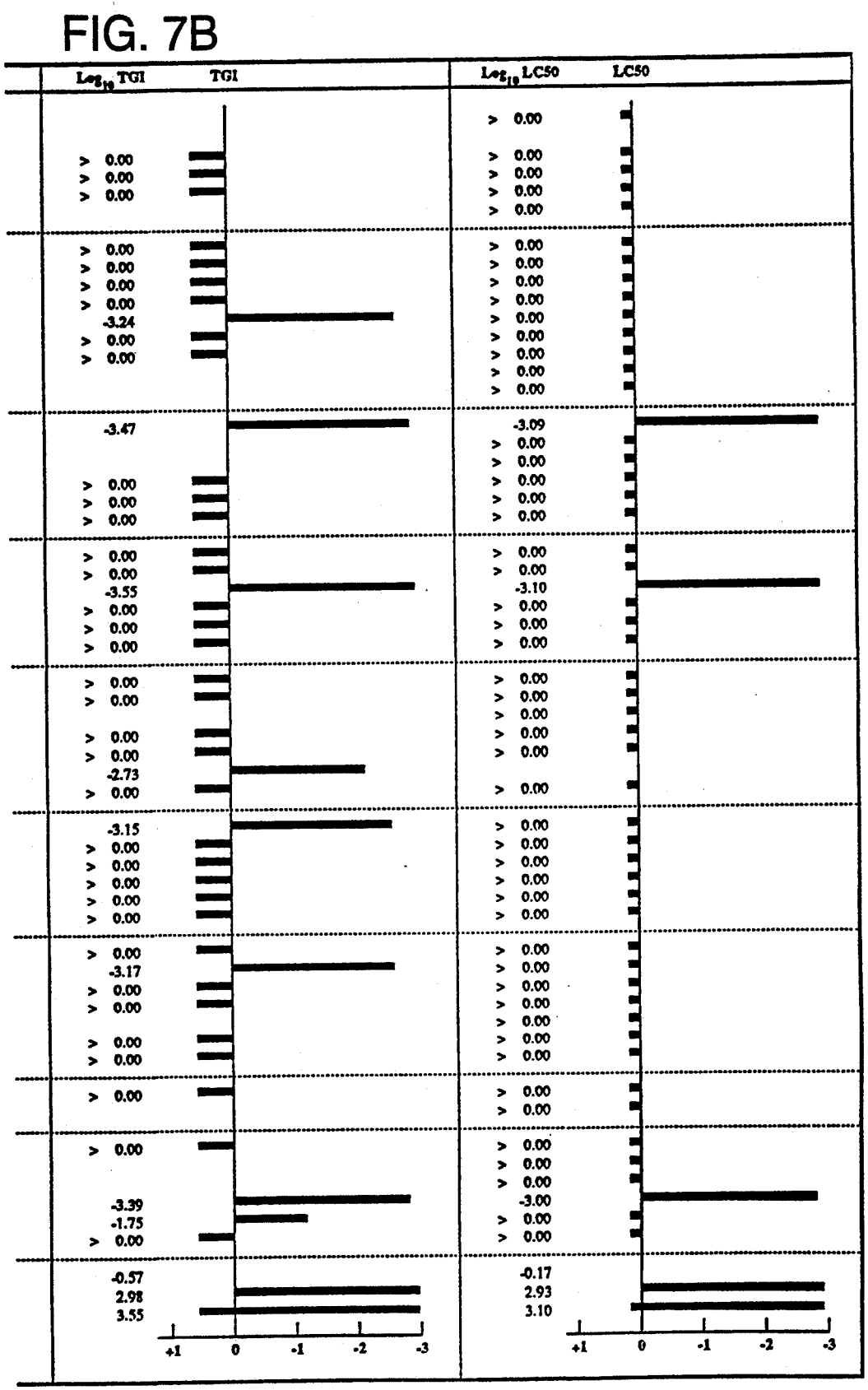
Figure 8A:
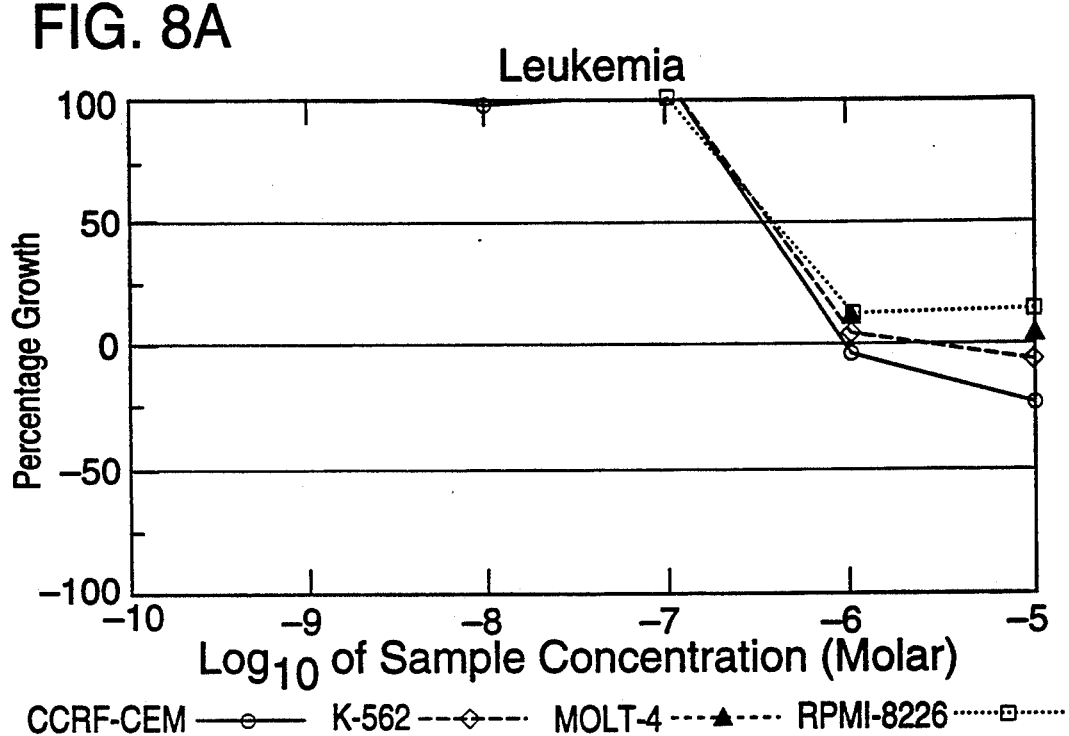
Figure 8B:
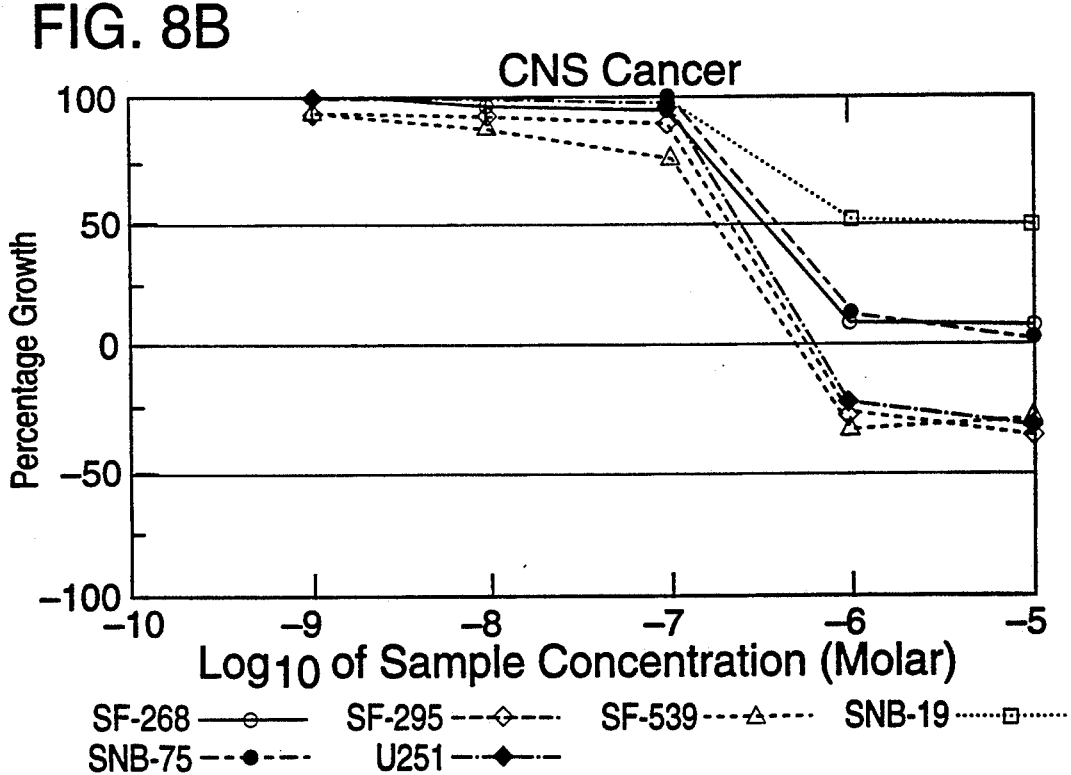
Figure 8I:
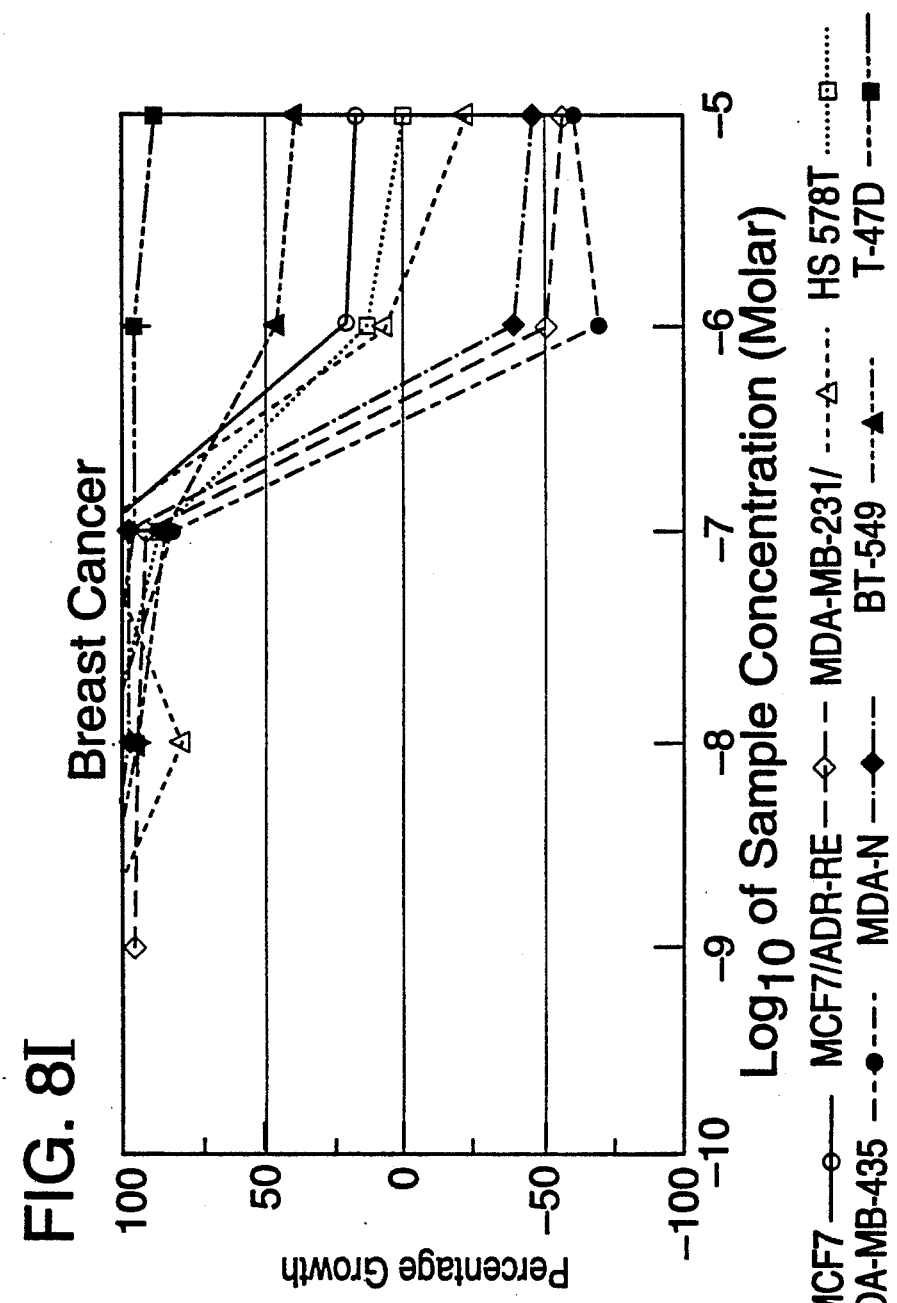

To produce data for the mean-graph format shown in FIG. 7, a concentration of the extract that produced a target level response was calculated for each cell line. Three different response parameters were evaluated. The first response parameter was the "$GI_{50}$," which is the concentration of the extract that produced an apparent 50% decrease in the number of tumor cells relative to the appropriate control (not exposed to extract) at the end of the incubation period. The second response parameter was the "TGI," which is the concentration at which the number of tumor cells remaining at the end of the incubation period substantially equaled the number of tumor cells existing at the start of the incubation period. The third response parameter was the "$LC_{50}$," which is the concentration of extract that caused an apparent 50 percent reduction in the number of tumor cells relative to the appropriate control (not exposed to extract) at the start of the incubation period.

In a typical $GI_{50}$ mean graph (e.g., left graph of FIG. 7), the relative position of the vertical reference line along the horizontal concentration axis is obtained by averaging the negative $\log_{10} GI_{50}$ values for all the cell lines tested against the extract. Horizontal bars are then plotted for the individual negative $\log_{10} GI_{50}$ values of each cell line relative to the vertical reference line. The $GI_{50}$ graph thus provides a characteristic fingerprint for the extract, displaying the individual cell lines that are proportionately more sensitive than average (bars extending to the right of the reference line) or proportionately less sensitive than average (bars extending to the left of the reference line). The length of a bar is proportional to the difference between the $\log_{10} GI_{50}$ value obtained with the particular cell line and the mean (represented by the vertical reference line). For example, for a given cell line, a bar extending three log units to the right of the mean reflects an individual cellular sensitivity $10^3$ times greater than the mean of all the cellular responses to the extract.

Similar mean graphs are shown in FIG. 7 for the TGI (middle graph) and $LC_{50}$ (right-hand graph) response parameters.

A computer program called COMPARE is used by the National Cancer Institute to explore similarities and differences in the mean graph fingerprint of the sample drug compared to mean graph fingerprints of compounds in the standard agent database. COMPARE is used to rank the similarity of the mean graph profile of the sample extract or drug to the patterns of all the other compounds in the NCI screening database or a defined subset thereof.

The data of these Examples were subjected to COMPARE analysis and the results are presented below in Table 1, showing correlation coefficients to the sample extract.

TABLE 1

| NSC | Hi Conc. | Correl. Coeff. | Drug Name |
|---|---|---|---|
| $GI_{50}$ | | | |
| 83265 | $1.25 \times 10^{-4}$ | 0.436 | S-trityl-L-cysteine |
| 153858 | $1.00 \times 10^{-4}$ | 0.423 | Maytansine |
| 368390 | $5.00 \times 10^{-3}$ | 0.400 | DUP785 (Brequinar) |
| 49842 | $2.50 \times 10^{-6}$ | 0.396 | Vinblastine sulfate |
| 7365 | $2.50 \times 10^{-4}$ | 0.391 | DON |
| 740 | $2.50 \times 10^{-4}$ | 0.369 | Methotrexate |
| 163501 | $1.00 \times 10^{-3}$ | 0.353 | AT-125 |
| 71851 | $5.00 \times 10^{-3}$ | 0.333 | A-TGDR |
| 366140 | $6.25 \times 10^{-4}$ | 0.330 | Pyrazoloacridine |
| 320846 | $1.25 \times 10^{-4}$ | 0.328 | Batracyclin |
| 352122 | $2.50 \times 10^{-4}$ | 0.326 | Trimetrexate |
| TGI | | | |

TABLE 1-continued

| NSC | Hi Conc. | Correl. Coeff. | Drug Name |
|---|---|---|---|
| 49842 | $2.50 \times 10^{-6}$ | 0.651 | Vinblastine sulfate |
| 67574 | $1.00 \times 10^{-3}$ | 0.611 | Vincristine sulfate |
| 332598 | $1.00 \times 10^{-9}$ | 0.576 | Rhizoxin |
| 153858 | $1.00 \times 10^{-4}$ | 0.530 | Maytansine |
| 157365 | $2.00 \times 10^{2}$ | 0.443 | Neocarzinostatin |
| 3053 | $2.50 \times 10^{-7}$ | 0.417 | Actinomycin D |
| 125973 | $2.50 \times 10^{-5}$ | 0.375 | Pacitaxel |
| 24559 | $1.25 \times 10^{-3}$ | 0.345 | Mitramycin |
| 349156 | $2.25 \times 10^{-4}$ | 0.318 | Pancratiastatin |
| 141537 | $1.00 \times 10^{-4}$ | 0.308 | Anguidine |
| 68075 | $5.00 \times 10^{-5}$ | 0.300 | Thalicarpine |
| LC$_{50}$ | | | |
| 95678 | $1.00 \times 10^{-3}$ | 0.646 | 3-HP |
| 125066 | $2.50 \times 10^{-5}$ | 0.520 | Bleomycin |
| 49842 | $2.50 \times 10^{-6}$ | 0.488 | Vinblastine sulfate |
| 32946 | $2.50 \times 10^{-3}$ | 0.465 | Methyl-GAG |
| 526417 | $7.50 \times 10^{-5}$ | 0.425 | Echinomycin |
| 153858 | $1.00 \times 10^{-4}$ | 0.412 | Maytansine |
| 83265 | $1.25 \times 10^{-4}$ | 0.405 | S-Trityl-L-Cysteine |
| 67574 | $1.00 \times 10^{-3}$ | 0.395 | Vincristine sulfate |
| 68075 | $5.00 \times 10^{-5}$ | 0.391 | Thalicarpine |
| 283162 | $1.25 \times 10^{-3}$ | 0.353 | Trimethyl-trimethylolmelamine |
| 58514 | $1.00 \times 10^{-4}$ | 0.340 | Chromomycin A3 |

The data in Table 1 indicate that the extract exhibits an antimitotic mode of action. This is because most of the drugs exhibiting mean-graph profiles that are similar to the extract (as tabulated in Table 1) are antimitotics.

EXAMPLES 62-121

Figure 9A:
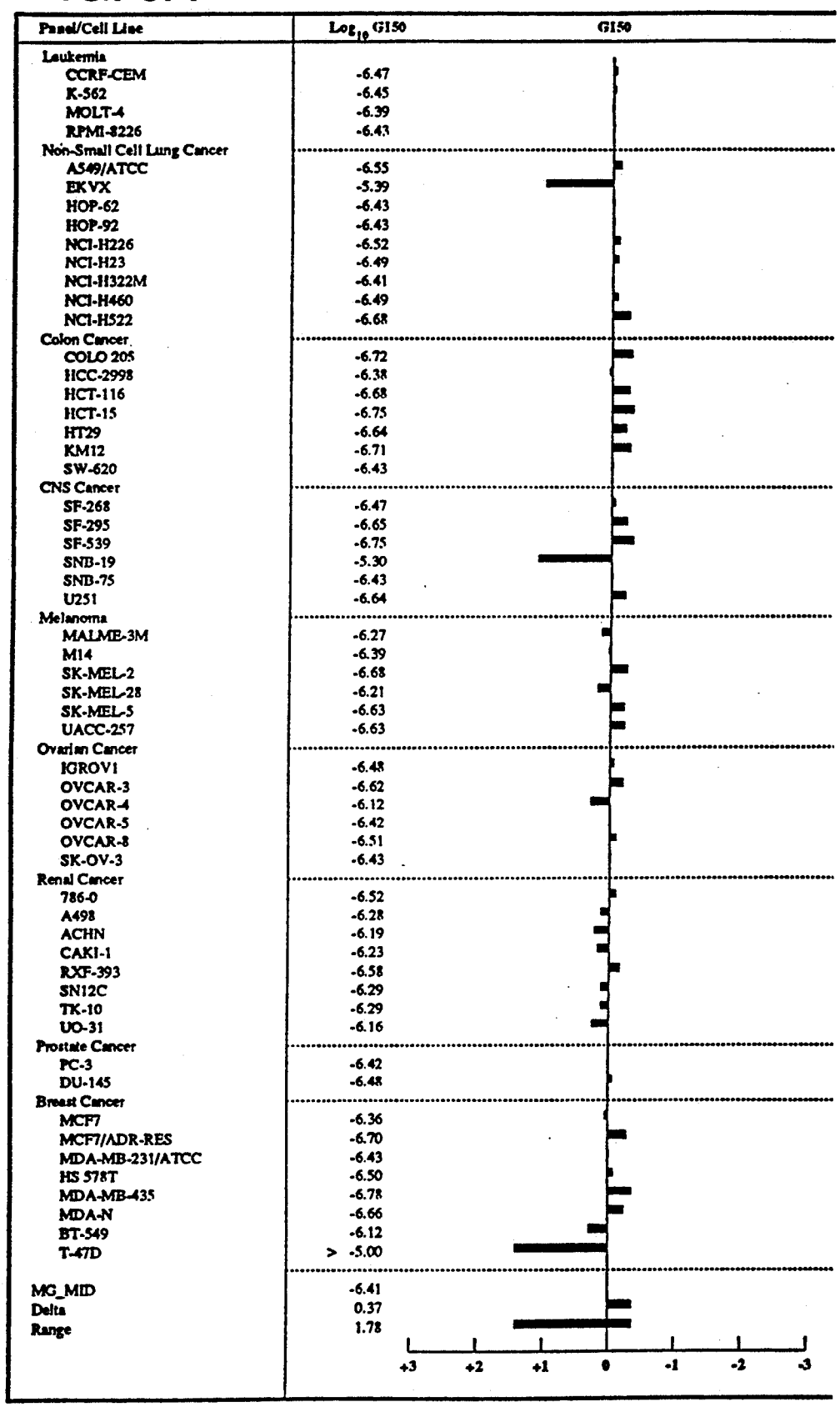
FIGS. 9A-9B show mean-plots of data from FIGS. 8A-8I, arranged similarly to the plots shown in FIGS. 7A-7B.
Figure 9B:
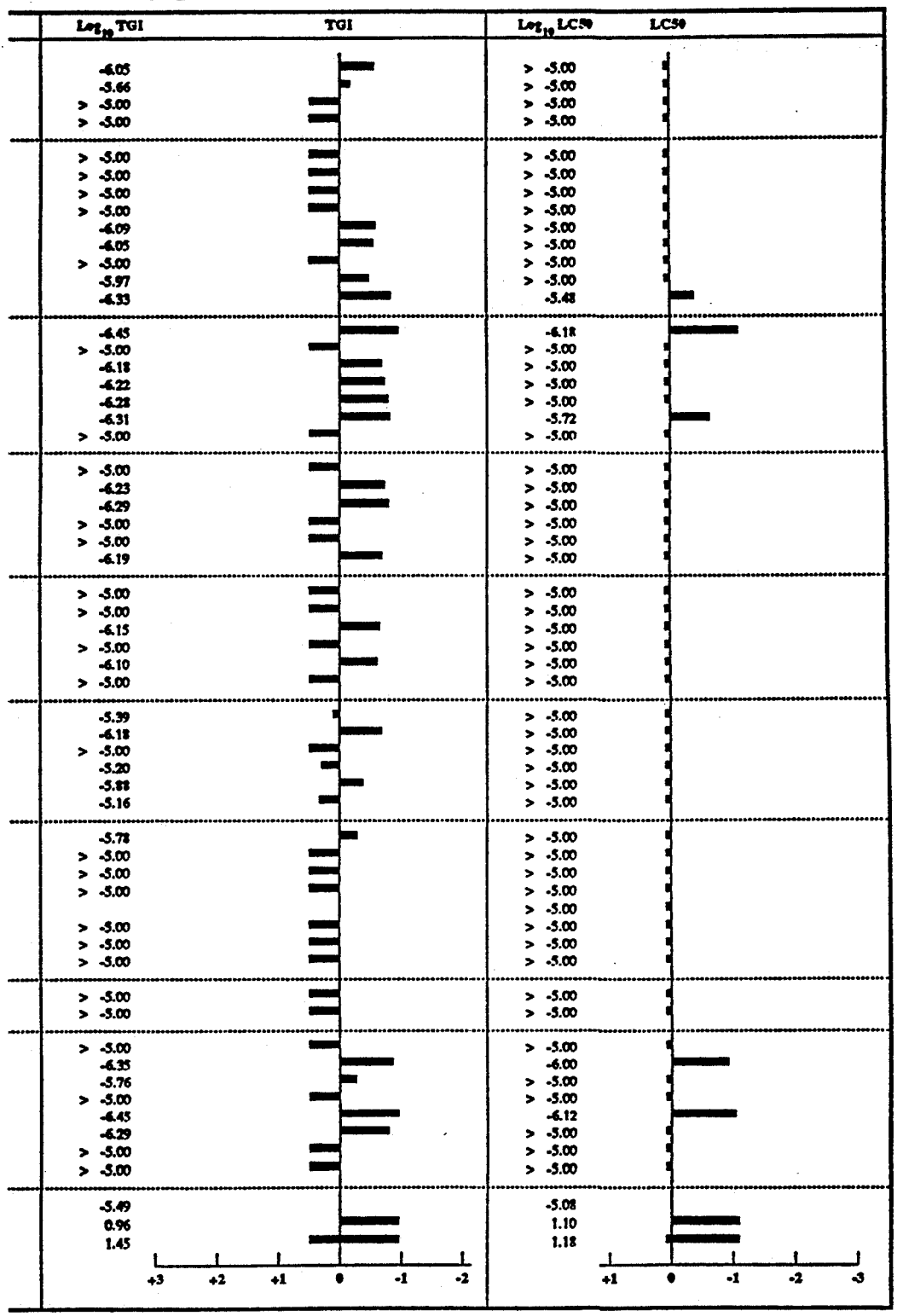
Figure 10H:
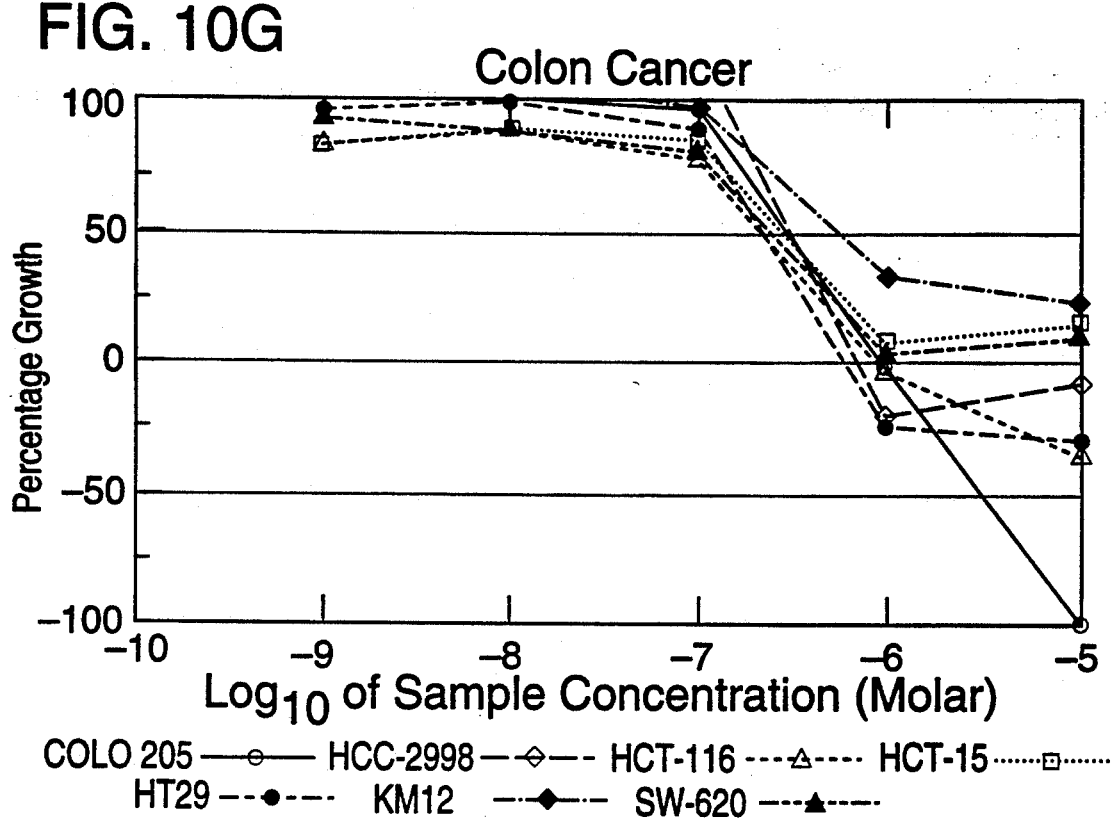
Figure 10H:
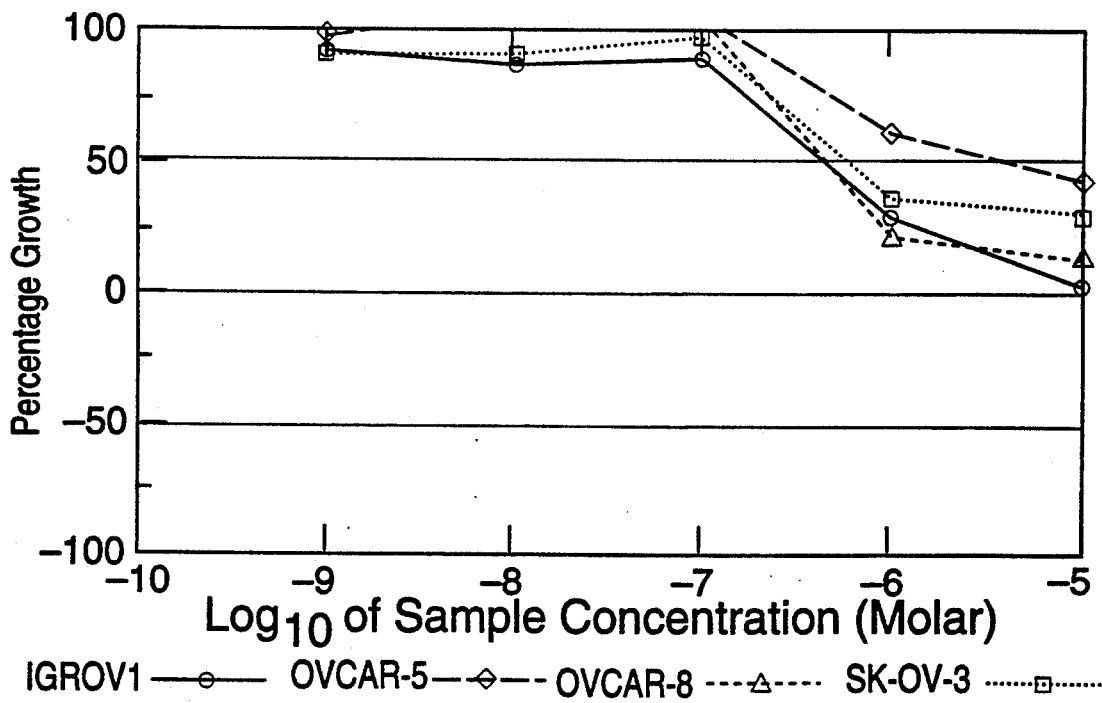

In these examples, purified Curacin A was tested according to the 60-cell line assay described above in Examples 2-61. Dose-response data are shown in FIGS. 8A-8I, and mean-plot data are shown in FIG. 9.

Compare data are set forth below in Table 2.

TABLE 2

| NSC | Hi Conc. | Correl. Coeff. | Drug Name |
|---|---|---|---|
| GI$_{50}$ | | | |
| 153858 | $1.00 \times 10^{-4}$ | 0.590 | Maytansine |
| 49842 | $2.50 \times 10^{-6}$ | 0.519 | Vinblastine sulfate |
| 125973 | $2.50 \times 10^{-5}$ | 0.431 | Paclitaxel |
| 752 | $2.50 \times 10^{-4}$ | 0.409 | Thioguanine |
| 755 | $7.50 \times 10^{-4}$ | 0.394 | 6-mercaptopurine |
| 104801 | $1.00 \times 10^{-2}$ | 0.383 | Cytembena |
| 71851 | $5.00 \times 10^{-3}$ | 0.381 | A-TGDR |
| 71261 | $1.25 \times 10^{-3}$ | 0.359 | B-TGDR |
| 264880 | $2.50 \times 10^{-3}$ | 0.351 | Dihydro-5-azacytidine |
| 67574 | $1.00 \times 10^{-3}$ | 0.344 | Vincristine sulfate |
| 740 | $2.50 \times 10^{-4}$ | 0.344 | Methotrexate |
| TGI | | | |
| 153858 | $1.00 \times 10^{-4}$ | 0.721 | Maytansine |
| 49842 | $2.50 \times 10^{-6}$ | 0.656 | Vinblastine sulfate |
| 67574 | $1.00 \times 10^{-3}$ | 0.640 | Vincristine sulfate |
| 332598 | $1.00 \times 10^{-9}$ | 0.541 | Rhizoxin |
| 83265 | $1.25 \times 10^{-4}$ | 0.413 | S-trityl-L-cysteine |
| 330500 | $5.00 \times 10^{-4}$ | 0.389 | Macbecin II |
| 125973 | $2.50 \times 10^{-5}$ | 0.369 | Paclitaxel |
| 157365 | $2.00 \times 10^{2}$ | 0.337 | Neocarzinostatin |
| 752 | $2.50 \times 10^{-4}$ | 0.329 | Thioguanine |
| 104801 | $1.00 \times 10^{-2}$ | 0.309 | Cytembena |
| 303812 | $5.00 \times 10^{-4}$ | 0.304 | Aphidicolin glycinate |
| LC50 | | | |

TABLE 2-continued

| NSC | Hi Conc. | Correl. Coeff. | Drug Name |
|---|---|---|---|
| 109229 | $2.50 \times 10^{-2}$ | 0.657 | L-asparaginase |
| 67574 | $1.00 \times 10^{-3}$ | 0.637 | Vincristine sulfate |
| 49842 | $2.50 \times 10^{-6}$ | 0.626 | Vinblastine sulfate |
| 71851 | $5.00 \times 10^{-3}$ | 0.563 | A-TGDR |
| 153858 | $1.00 \times 1.^{-4}$ | 0.561 | Maytansine |
| 366241 | $1.00 \times 10^{-4}$ | 0.508 | Bis-pyridocarbazolium DMS |
| 752 | $2.50 \times 10^{-4}$ | 0.500 | Thioguanine |
| 71261 | $1.25 \times 10^{-3}$ | 0.437 | B-TGDR |
| 83265 | $1.25 \times 10^{-4}$ | 0.413 | S-Trityl-L-cysteine |
| 32946 | $2.50 \times 10^{-3}$ | 0.400 | Methyl-GAG |
| 602668 | $1.00 \times 10^{-3}$ | 0.391 | Carmethizole |

Again, these data indicate that Curacin A functions as an antimitotic and has a mode of action that is similar to a number of conventional antineoplastics.

EXAMPLES 122-181

Figure 11A:
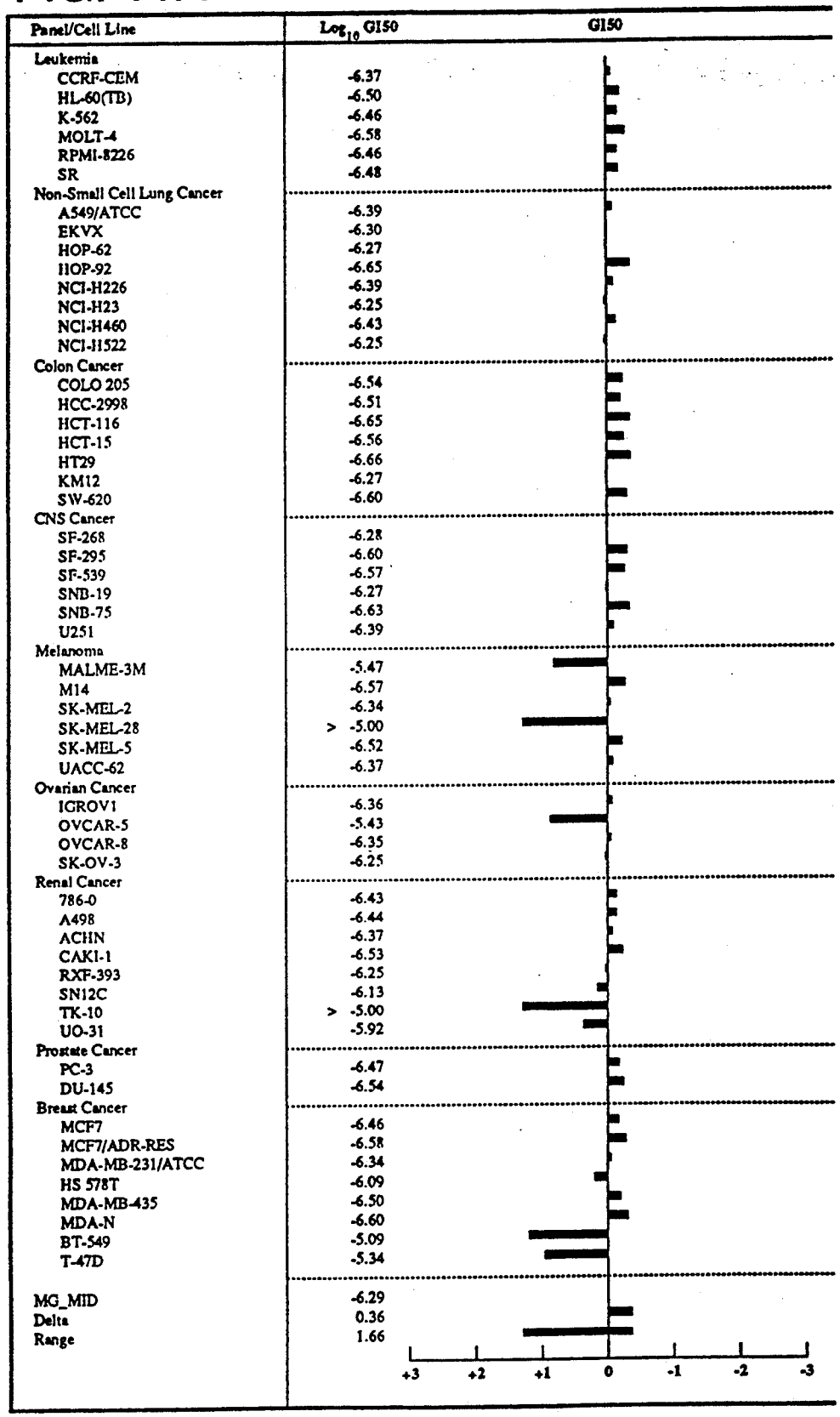
FIGS. 11A-11B show mean-plots of data from FIGS. 10A-10I, arranged similarly to the plots shown in FIGS. 7A-7B.
Figure 11B:
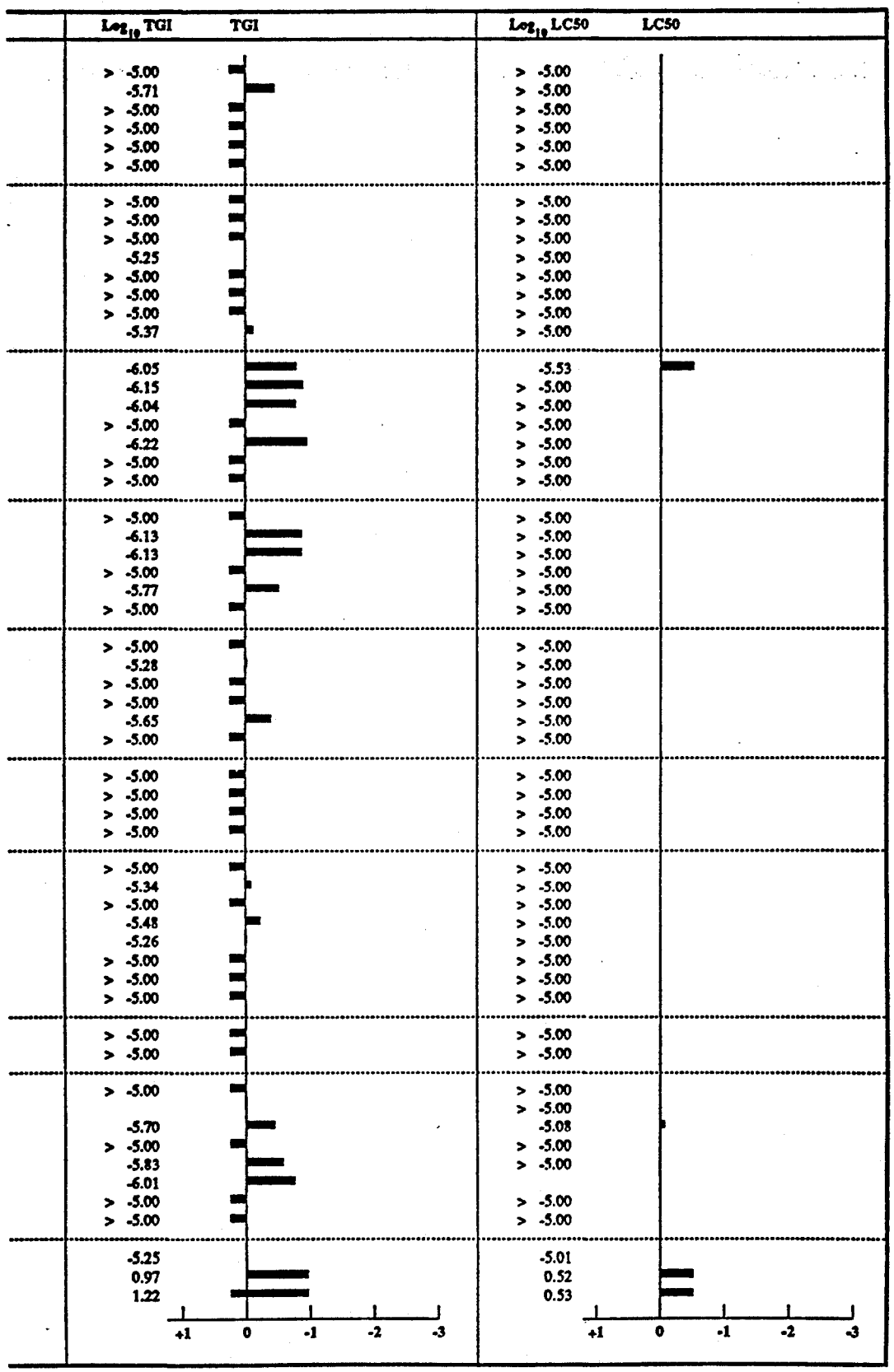

In these Examples, purified Curacin A was again tested according to the 60 cell-line assay described above in Examples 2-61. Dose-response data are shown in FIGS. 10A-10I, and mean-plot data are shown in FIG. 11.

What is claimed is:

1. A compound of the formula:

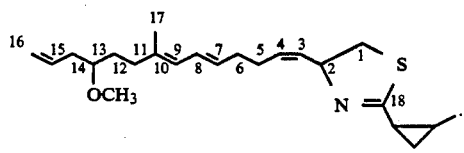

2. Curacin A and stereoisomers thereof.

3. A composition of matter comprising a pharmaceutically inert carrier and a compound selected from a group consisting of Curacin A and stereoisomers thereof, the compound being present in the composition in an amount sufficient to act as an antiproliferative agent to living cells.

4. A method of treating an animal subject to inhibit the proliferation of living cells in the subject, the method comprising administering to the subject an effective amount of a formulation comprising a compound selected from a group consisting of Curacin A and stereoisomers thereof.

5. A method for inhibiting proliferation of living cells comprising contacting the cells with an amount of a formulation comprising a compound selected from a group consisting of Curacin A and stereoisomers thereof, the amount being sufficient to inhibit proliferation of the cells compared to otherwise identical control cells not contacted with the formulation.

6. A method for reducing a population of arthropods, comprising contacting the population with a formulation comprising an amount of a compound selected from a group consisting of Curacin A and stereoisomers thereof, the amount being sufficient to reduce the population compared to an otherwise control population not contacted with the formulation.

* * * * *

UNITED STATES PATENT AND TRADEMARK OFFICE
CERTIFICATE OF CORRECTION

PATENT NO. : 5,324,739
DATED : June 28, 1994
INVENTOR(S) : GERWICK ET AL.

It is certified that error appears in the above-identified patent and that said Letters Patent is hereby corrected as shown below:

Column 3, line 18, --nuclear-- should be inserted after
    "proton".

Signed and Sealed this

Tenth Day of September, 1996

Attest:

BRUCE LEHMAN

Attesting Officer

Commissioner of Patents and Trademarks